(12) United States Patent
Fujiwara et al.

(10) Patent No.: US 7,943,373 B2
(45) Date of Patent: May 17, 2011

(54) TELOMELYSIN/GFP-EXPRESSING RECOMBINANT VIRUS

(75) Inventors: Toshiyoshi Fujiwara, Okayama (JP); Noriaki Tanaka, Okayama (JP); Satoru Kyo, Kanazawa (JP); Hiroyuki Mizuguchi, Minoo (JP); Takao Hayakawa, Tokyo (JP)

(73) Assignee: Oncolys Biopharma, Inc., Tokyo (JP)

( * ) Notice: Subject to any disclaimer, the term of this patent is extended or adjusted under 35 U.S.C. 154(b) by 156 days.

(21) Appl. No.: 11/158,479

(22) Filed: Jun. 21, 2005

(65) Prior Publication Data

US 2006/0067890 A1    Mar. 30, 2006

(30) Foreign Application Priority Data

Sep. 29, 2004    (JP) ................. 2004-285383

(51) Int. Cl.
*C12N 15/63* (2006.01)
*C12P 19/34* (2006.01)
(52) U.S. Cl. ............... 435/320.1; 435/91.4; 435/350
(58) Field of Classification Search ............. 435/320.1
See application file for complete search history.

(56) References Cited

U.S. PATENT DOCUMENTS

2004/0156830 A1  8/2004  Udono
2006/0239967 A1  10/2006  Fujiwara et al.

FOREIGN PATENT DOCUMENTS

JP    2004-033186    2/2004
JP    2004-236505    8/2004

OTHER PUBLICATIONS

Iriving et al. Cancer Gene Ther. 2004, vol. 11, pp. 174-185.*
Rivera et al. Virol. 2004, vol. 320, pp. 121-134.*
Randrianarison-Jewtoukoff et al. Biologicals, 1995, vol. 23, pp. 145-157.*
Wirth et al. Cancer Res. Jun. 2003, vol. 63, pp. 3181-3188.*
Kishimoto et al. Nature Medicine, 2005, vol. 12, No. 10, pp. 1213-1219.*
Feit et al. 2003, J. Pat. Trade. Off. Soc., vol. 85, No. 1, pp. 5-21.*
Mizuguchi, Basic Study for Next-generation Gene Therapy Products, Pharmaceutical Magazine 123(9) 761-771 (English Translation) (2003).
Verma, I. M. et al. "Gene Therapy—Promises, Problems, and Prospects." Nature. vol. 389, p. 239-242 (1997).
Raper, S. E. et al. "Fatal Systemic Inflammatory Response Syndrome in a Omithine Transcarbamylase Deficient Patient Following Adenoviral Gene Transfer." Molecular Genetics and Metabolism. vol. 80, Issues 1-2, p. 148-158 (2003).
Kishimoto Hiroyuki et al: "In Vivo Imaging of Lymph Node Metastasis iwth Telomerase-Specific Replication-Selective Adenovirus." Nature Medicine, vol. 12, No. 10, Oct. 2006 , pp. 1213-1219.
Nemunaitis et al., "Enhanced Oncolytic Potency of Replicative Adenovirus Expressing p53" (Drug Resistance Updates) 2003, vol. 7, pp. 5-7.
Sauthoff et al., "Late Expression of p53 from a Replicating Adenovirus Improves Tumor Cell Killing and Is More Tumor Cell Specific than Expression of the Adenoviral Death Protein" (Human Gene Therapy) 2001, vol. 13, pp. 1859-1871.
Kojima et al., "A Simple Biological Imaging System for Detecting Viable Human Circulating Tumor Cells" J. Clin. Invest. (Oct. 2009) vol. 119 (No. 10), pp. 3172-3181.
"Cancer: Green Surgery" Science (Sep. 11, 2009) vol. 325 (No. 5946), p. 1321.
Kishimoto et al., "In Vivo Internal Tumor Illumination by Telomerase-Dependent Adenoviral GFP for Precise Surgical Navigation," Proc. Natl. Acad. Sci. U.S.A. (Aug. 25, 2009) vol. 106 (No. 34), pp. 14514-15417.
Umeoka, T., et al., "Vizualization of Intrathoracically Disseminated Solid Tumors in Mice with Optical Imaging by Telomerase-Specific Amplification of a Transferred Green Fluorescent Protein Gene," Cancer Research, vol. 64, Sep. 1, 2004, p. 6259-6265.
Mizuguchi, H.,"Basic Study for Next-Generation Gene Therapy Products," Yakugaku Zasshi, vol. 123, 2003, p. 761-771.
Jacob, D., et al., Suppressing Orthotopic Pancreatic Tumor Growth with a Fiber-Modified Adenovector Expressing the TRAIL Gene from the Human Telomerase Reverse Transcriptase Promoter, Clinical Cancer Research, vol. 10, May 15, 2004, p. 3535-3541.
Kawashima, T., et al., "Telomerase-Specific Replication-Selective Virotherapy for Human Cancer," Clinical Cancer Research, vol. 10, Jan. 1, 2004, p. 285-292.
Mizuguchi, H., et al., "In Vitro Ligation-Based Cloning of Foreign DNAs into the E3 and E1 Deletion Regions for Generation of Recombinant Adenovirus Vectors," BioTechniques, vol. 30, 2001, p. 1112-1116.
International Search Report dated Nov. 8, 2005 issued for corresponding International Patent Application No. PCT/JP2005/018401.

\* cited by examiner

*Primary Examiner* — Bao Li
(74) *Attorney, Agent, or Firm* — Fish & Richardson P.C.

(57) ABSTRACT

The present invention provides a reagent for cancer cell detection or cancer diagnosis. The present invention relates to a reagent for cancer cell detection, comprising a recombinant virus where a replication cassette comprising a promoter from human telomerase, an E1A gene, an IRES sequence and an E1B gene in this order is integrated in E1 region of the viral genome and a labeling cassette comprising a gene encoding a labeling protein and a promoter capable of regulating the expression of the gene encoding the labeling protein is integrated in E3 region of the viral genome.

3 Claims, 20 Drawing Sheets
(20 of 20 Drawing Sheet(s) Filed in Color)

SEQUENCE LISTING

```
<160> NUMBER OF SEQ ID NOS: 10

<210> SEQ ID NO 1
<211> LENGTH: 455
<212> TYPE: DNA
```

<213> ORGANISM: human

<400> SEQUENCE: 1

```
tggcccctcc ctcgggttac cccacagcct aggccgattc gacctctctc cgctggggcc    60
ctcgctggcg tccctgcacc ctgggagcgc gagcggcgcg cgggcgggga agcgcggccc   120
agacccccgg gtccgcccgg agcagctgcg ctgtcggggc caggccgggc tcccagtgga   180
ttcgcgggca cagacgccca ggaccgcgct ccccacgtgg cggagggact ggggacccgg   240
gcacccgtcc tgcccttca ccttccagct ccgcctcctc cgcgcggacc ccgccccgtc    300
ccgacccctc ccgggtcccc ggcccagccc ctccgggcc ctcccagccc ctcccccttcc   360
tttccgcggc cccgccctct cctcgcggcg cgagtttcag gcagcgctgc gtcctgctgc   420
gcacgtggga agccctggcc ccggccaccc ccgcg                              455
```

<210> SEQ ID NO 2
<211> LENGTH: 899
<212> TYPE: DNA
<213> ORGANISM: adenovirus

<400> SEQUENCE: 2

```
acaccgggac tgaaaatgag acatattatc tgccacggag gtgttattac cgaagaaatg    60
gccgccagtc ttttggacca gctgatcgaa gaggtactgg ctgataatct tccacctcct   120
agccattttg aaccacctac ccttcacgaa ctgtatgatt tagacgtgac ggccccgaa    180
gatcccaacg aggaggcggt tcgcagatt tttcccgact ctgtaatgtt ggcggtgcag    240
gaagggattg acttactcac ttttccgccg gcgcccggtt ctccggagcc gcctcacctt   300
tcccggcagc ccgagcagcc ggagcagaga gccttgggtc cggtttctat gccaaacctt   360
gtaccggagg tgatcgatct tacctgccac gaggctggct ttccacccag tgacgacgag   420
gatgaagagg gtgaggagtt tgtgttagat tatgtggagc accccgggca cggttgcagg   480
tcttgtcatt atcaccggag gaatacgggg gacccagata ttatgtgttc gctttgctat   540
atgaggacct gtggcatgtt tgtctacagt cctgtgtctg aacctgagcc tgagcccgag   600
ccagaaccgg agcctgcaag acctacccgc cgtcctaaaa tggcgcctgc tatcctgaga   660
cgcccgacat cacctgtgtc tagagaatgc aatagtagta cggatagctg tgactccggt   720
ccttctaaca cacctcctga gatacacccg gtggtcccgc tgtgccccat taaaccagtt   780
gccgtgagag ttggtgggcg tcgccaggct gtggaatgta tcgaggactt gcttaacgag   840
cctgggcaac ctttggactt gagctgtaaa cgccccaggc cataaggtgt aaacctgtg    899
```

<210> SEQ ID NO 3
<211> LENGTH: 1823
<212> TYPE: DNA
<213> ORGANISM: adenovirus

<400> SEQUENCE: 3

```
ctgacctcat ggaggcttgg gagtgtttgg aagatttttc tgctgtgcgt aacttgctgg    60
aacagagctc taacagtacc tcttggtttt ggaggtttct gtggggctca tcccaggcaa   120
agttagtctg cagaattaag gaggattaca gtgggaatt tgaagagctt ttgaaatcct   180
gtggtgagct gtttgattct ttgaatctgg gtcaccaggc gcttttccaa gagaaggtca   240
tcaagacttt ggattttttcc acaccggggc gcgctgcggc tgctgttgct tttttgagtt   300
ttataaagga taaatggagc gaagaaaccc atcgagcgg ggggtacctg ctggatttttc   360
tggccatgca tctgtggaga gcggttgtga gacacaagaa tcgcctgcta ctgttgtctt   420
```

-continued

```
ccgtccgccc ggcgataata ccgacggagg agcagcagca gcagcaggag gaagccaggc    480
ggcggcggca ggagcagagc ccatggaacc cgagagccgg cctggaccct cgggaatgaa    540
tgttgtacag gtggctgaac tgtatccaga actgagacgc attttgacaa ttacagagga    600
tgggcagggg ctaaaggggg taaagaggga gcgggggggct tgtgaggcta cagaggaggc    660
taggaatcta gcttttagct taatgaccag acaccgtcct gagtgtatta cttttcaaca    720
gatcaaggat aattgcgcta atgagcttga tctgctggcg cagaagtatt ccatagagca    780
gctgaccact tactggctgc agccagggga tgattttgag gaggctatta gggtatatgc    840
aaaggtggca cttaggccag attgcaagta caagatcagc aaacttgtaa atatcaggaa    900
ttgttgctac atttctggga acggggccga ggtggagata gatacggagg atagggtggc    960
ctttagatgt agcatgataa atatgtggcc gggggtgctt ggcatggacg gggtggttat   1020
tatgaatgta aggtttactg gccccaattt tagcggtacg gttttcctgg ccaataccaa   1080
ccttatccta cacggtgtaa gcttctatgg gtttaacaat acctgtgtgg aagcctggac   1140
cgatgtaagg gttcggggct gtgcctttta ctgctgctgg aaggggtgg tgtgtcgccc    1200
caaaagcagg gcttcaatta agaaatgcct ctttgaaagg tgtaccttgg gtatcctgtc   1260
tgagggtaac tccagggtgc gccacaatgt ggcctccgac tgtggttgct tcatgctagt   1320
gaaaagcgtg gctgtgatta agcataacat ggtatgtggc aactgcgagg acagggcctc   1380
tcagatgctg acctgctcgg acggcaactg tcacctgctg aagaccattc acgtagccag   1440
ccactctcgc aaggcctggc cagtgtttga gcataacata ctgacccgct gttccttgca   1500
tttgggtaac aggaggggg tgttcctacc ttaccaatgc aatttgagtc acactaagat    1560
attgcttgag cccgagagca tgtccaaggt gaacctgaac ggggtgtttg acatgaccat   1620
gaagatctgg aaggtgctga ggtacgatga gacccgcacc aggtgcagac cctgcgagtg   1680
tggcggtaaa catattagga accagccgt gatgctggat gtgaccgagg agctgaggcc    1740
cgatcacttg gtgctggcct gcacccgcgc tgagtttggc tctagcgatg aagatacaga   1800
ttgaggtact gaaatgtgtg ggc                                            1823
```

<210> SEQ ID NO 4
<211> LENGTH: 605
<212> TYPE: DNA
<213> ORGANISM: adenovirus

<400> SEQUENCE: 4

```
tgcatctagg gcggccaatt ccgcccctct ccctccccc cccctaacgt tactggccga     60
agccgcttgg aataaggccg gtgtgcgttt gtctatatgt gattttccac catattgccg    120
tcttttggca atgtgagggc ccggaaacct ggccctgtct tcttgacgag cattcctagg    180
ggtctttccc ctctcgccaa aggaatgcaa ggtctgttga atgtcgtgaa ggaagcagtt    240
cctctggaag cttcttgaag acaaacaacg tctgtagcga ccctttgcag gcagcggaac    300
cccccacctg gcgacaggtg cctctgcggc caaaagccac gtgtataaga tacacctgca    360
aaggcggcac aaccccagtg ccacgttgtg agttggatag ttgtggaaag agtcaaatgg    420
ctctcctcaa gcgtattcaa caaggggctg aaggatgccc agaaggtacc ccattgtatg    480
ggatctgatc tggggcctcg gtgcacatgc tttacatgtg tttagtcgag gttaaaaaaa    540
cgtctaggcc ccccgaacca cggggacgtg gttttccttt gaaaaacacg atgataagct    600
tgcca                                                                605
```

```
<210> SEQ ID NO 5
<211> LENGTH: 20
<212> TYPE: DNA
<213> ORGANISM: artificial
<220> FEATURE:
<223> OTHER INFORMATION: primer

<400> SEQUENCE: 5
acaccgggac tgaaaatgag                                              20

<210> SEQ ID NO 6
<211> LENGTH: 21
<212> TYPE: DNA
<213> ORGANISM: artificial
<220> FEATURE:
<223> OTHER INFORMATION: primer

<400> SEQUENCE: 6
cacaggttta caccttatgg c                                            21

<210> SEQ ID NO 7
<211> LENGTH: 20
<212> TYPE: DNA
<213> ORGANISM: artificial
<220> FEATURE:
<223> OTHER INFORMATION: primer

<400> SEQUENCE: 7
ctgacctcat ggaggcttgg                                              20

<210> SEQ ID NO 8
<211> LENGTH: 21
<212> TYPE: DNA
<213> ORGANISM: artificial
<220> FEATURE:
<223> OTHER INFORMATION: primer

<400> SEQUENCE: 8
gcccacacat ttcagtacct c                                            21

<210> SEQ ID NO 9
<211> LENGTH: 20
<212> TYPE: DNA
<213> ORGANISM: artificial
<220> FEATURE:
<223> OTHER INFORMATION: primer

<400> SEQUENCE: 9
cctgtgtcta gagaatgcaa                                              20

<210> SEQ ID NO 10
<211> LENGTH: 20
<212> TYPE: DNA
<213> ORGANISM: artificial
<220> FEATURE:
<223> OTHER INFORMATION: primer

<400> SEQUENCE: 10
acagctcaag tccaaaggtt                                              20
```

US 7,943,373 B2

TELOMELYSIN/GFP-EXPRESSING RECOMBINANT VIRUS

INCORPORATION BY REFERENCE

The present application claims priority under 35 U.S.C. §119 to Japanese Patent Application No. 2004-285383 filed on Sep. 29, 2004 in the Japanese language.

BACKGROUND OF THE INVENTION

The present invention relates to a reagent for detecting cancer cells or diagnosing cancers, and a cell death-inducing agent.

Telomerase activity is often enhanced in malignantly transformed cells or immortalized cell strains, whereas telomerase activity is hardly detected in normal somatic cells excluding such as germ line cells, blood lineage cells and epithelial cells. Therefore, attempts to detect cancer using telomerase activity as an indicator have been made (Shay J W, Zou Y, Hiyama E, Wright W E. Telomerase and Cancer. Hum Mol Genet 10 (7): 677-85, 2001).

On the other hand, detection of cancer tissues and metastatic lymph nodes in vivo has been studied eagerly in the field of diagnostic imaging. For example, biological diagnosis with PET and image analysis fully utilizing neural network have been reported. Further, investigations into the anti-tumor activity and safety of replication-selective viruses have been reported (DeWeese T L, van der Poel H, Li S, Mikhak B, Drew R, Goemann M, Hamper U, DeJong R, Detorie N, Rodriguez R, Haulk T, DeMarzo A M, Piantadosi S, Yu D C, Chen Y, Henderson D R, Carducci M A, Nelson W G, Simons J W. A phase I trial of CV706, "A replication-competent, PSA selective oncolytic adenovirus, for the treatment of locally recurrent prostate cancer following radiation therapy", Cancer Res 61(20):7464-72, 2001). The present inventors have also found that infecting cancer cells with a virus having a telomerase promoter and replication ability can kill the cancer cells by viral replication (Kawashima T, Kagawa S, Kobayashi N, Shirakiya Y, Umeoka T, Teraishi F, Taki M, Kyo S, Tanaka N, and Fujiwara T., Related Articles, Links Abstract "Telomerase-specific replication-selective virotherapy for human cancer", Clin Cancer Res 10(1):285-92, 2004).

However, in situ cancer detection system during surgical operation has not yet been developed because of the difficulty in targeting cancer cells. Further, no research has been known to date in which the living body is infected with a virus and the viral kinetics within cancer cells is actually applied to visualization of cancer tissues.

SUMMARY OF THE INVENTION

It is an object of the present invention to provide a reagent for detecting cancer cells or diagnosing cancers, and a cell death-inducing agent, which are capable of visualizing cancer cells not only in vitro but also in vivo.

As a result of intensive and extensive researches toward the solution of the above problems, the present inventors have found that it is possible to detect cancer cells with extremely high sensitivity and even in vivo, by integrating a gene encoding a fluorescence labeling protein in E3 region of a viral genome and integrating a replication cassette comprising a human telomerase promoter, an E1A gene, an IRES sequence and an E1B gene in this order in E1 region, and then expressing both cassettes. Thus, the present invention has been achieved.

The present invention relates to the following.

(1) A reagent for cancer cell detection, comprising a recombinant virus where a replication cassette comprising a promoter from human telomerase, an E1A gene, an IRES sequence and an E1B gene in this order is integrated in E1 region of the viral genome and a labeling cassette comprising a gene encoding a labeling protein and a promoter capable of regulating the expression of the gene encoding the labeling protein is integrated in E3 region of the viral genome.

(2) A reagent for cancer diagnosis, comprising a recombinant virus where a replication cassette comprising a promoter from human telomerase, an E1A gene, an IRES sequence and an E1B gene in this order is integrated in E1 region of the viral genome and a labeling cassette comprising a gene encoding a labeling protein and a promoter capable of regulating the expression of the gene encoding the labeling protein is integrated in E3 region of the viral genome.

In (1) and (2) above, these reagents may be used in in vivo detection, diagnosis or navigation surgery. As a specific example of the promoter from human telomerase, hTERT promoter may be given. As a specific example of the labeling protein, GFP may be given. As the promoter capable of regulating the expression of a gene encoding this labeling protein, a cytomegalovirus promoter may be used, for example. As the virus, an adenovirus may be used, for example.

(3) A cell death-inducing agent, comprising a recombinant virus where a replication cassette comprising a promoter from human telomerase, an E1A gene, an IRES sequence and an E1B gene in this order is integrated in E1 region of the viral genome and a cell death-inducing cassette comprising a gene encoding a protein associated with cell death induction and a promoter capable of regulating the expression of the gene encoding the protein associated with cell death induction is integrated in E3 region of the viral genome.

In this cell death-inducing agent, the promoter from human telomerase may be hTERT promoter. Examples of proteins associated with cell death induction include immunity-associated proteins, apoptosis-inducing proteins and telomerase-associated proteins. More specifically, PA28 may be given as an immunity-associated protein; TRAIL may be given as an apoptosis-inducing protein; and AU5 may be given as a telomerase-associated protein. The promoter capable of regulating the expression of a protein associated with cell death induction may be a cytomegalovirus promoter; and the virus may be an adenovirus. As a cell of the present invention, a cancer cell may be used.

(4) A method of detecting cancer cells, comprising infecting cancer cells with the reagent of (1) above and detecting the fluorescence emitted by the cancer cells.

(5) A method of cancer diagnosis, comprising infecting cancer cells with the reagent of (2) above and detecting the fluorescence emitted by the cancer cells.

(6) A method of inducing cell death in a target cell, comprising infecting the target cell with the cell death-inducing agent of (3) above.

According to the present invention, a reagent for detecting cancer cells or for diagnosing cancers, and a cell death-inducing agent are provided. Since the reagent of the present invention is capable of detecting cancer cells with extremely high sensitivity even in vivo, the reagent is useful in the so-called navigation surgery or the like.

BRIEF DESCRIPTION OF THE DRAWINGS

The patent or application file contains at least one drawing executed in color. Copies of this patent or patent application publication with color drawing(s) will be provided by Office upon request and payment of the necessary fee.

DETAILED DESCRIPTION OF THE INVENTION

Hereinbelow, the present invention will be described in detail.
1. Reagent for Cancer Cell Detection and Detection Method The present invention relates to a reagent for cancer diagnosis, comprising a recombinant virus where a replication cassette comprising a promoter from human telomerase, an E1A gene, an IRES sequence and an E1B gene in this order is integrated in E1 region of the viral genome and a labeling cassette comprising a gene encoding a labeling protein and a promoter capable of regulating the expression of the gene encoding the labeling protein is integrated in E3 region of the viral genome. Further, the present invention relates to a method of detecting cancer cells, comprising infecting cancer cells with the reagent and detecting the fluorescence emitted by the cancer cells. In the present invention, the term "recombinant virus" means a virus in which the replication cassette and the labeling cassette described later are integrated in the genome. The virus used in the present invention is not particularly limited, but an adenovirus is preferable from the viewpoint of safety. Among adenovirus species, type 5 adenovirus is especially preferable mainly because it is easy to handle.

Figure 1:
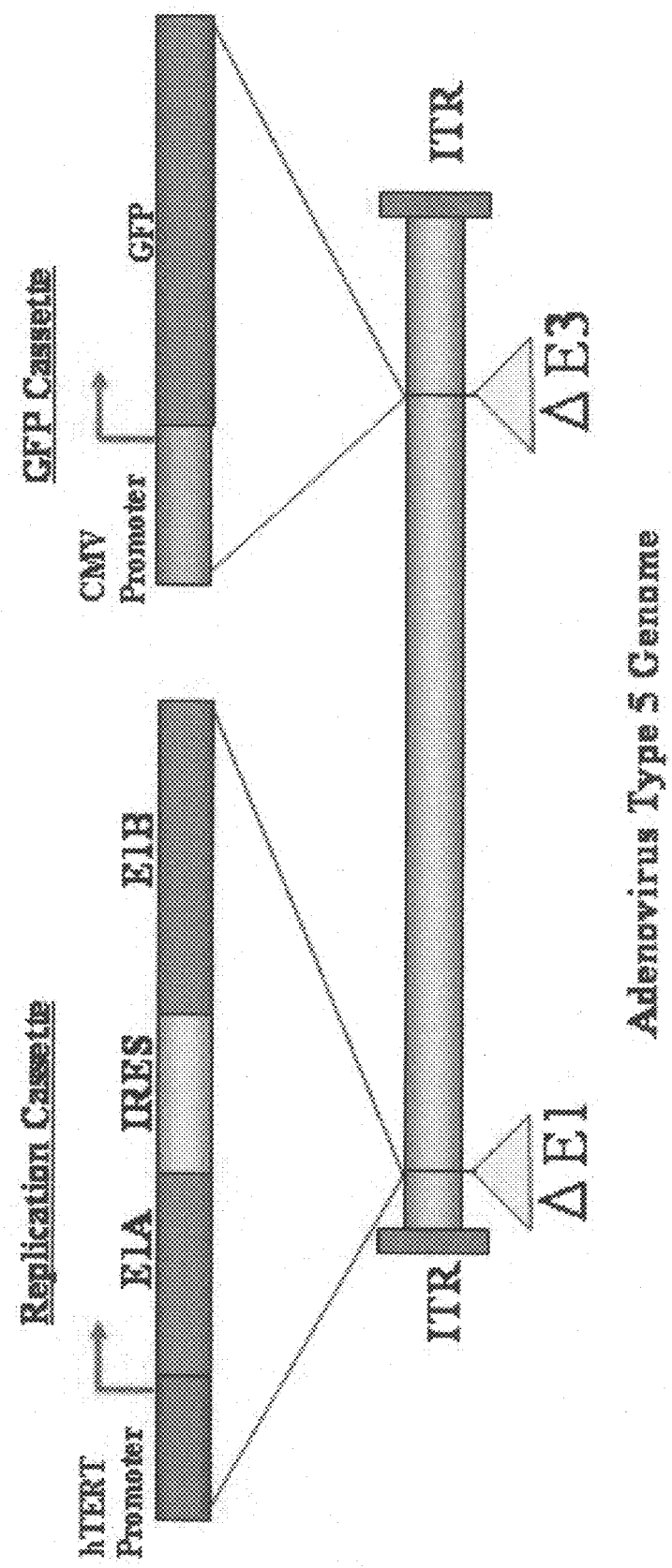
FIG. 1 is a diagram showing the structure of Telomelysin-GFP.

The recombinant virus used in the present invention has a replication cassette integrated in E1 region of the genome and a labeling cassette integrated in E3 region of the genome. The replication cassette comprises a promoter from human telomerase, an E1A gene, an IRES sequence and an E1B gene in this order. The E1A gene, IRES sequence and E1B gene are driven by the human telomerase promoter, which results in cancer cell-specific and telomerase-specific proliferation/replication of the virus. The labeling cassette comprises a promoter and a gene encoding a labeling protein. For example, the gene encoding the labeling protein is driven by a CMV (cytomegalovirus) promoter (FIG. 1).

The "telomerase promoter" determines the transcription initiation site for telomerase and directly regulates the frequency of transcription. Telomerase is an enzyme that maintains the length of telomeres, standing against the shortening of telomeres at the time of replication of eukaryotic chromosomes. The kind of such telomerase promoter is not particularly limited. For example, the promoter of human telomerase reverse transcriptase (hTERT) is preferable. A number of transcription factor-binding sequences are confirmed in a 1.4 kbp region upstream of the 5' end of hTERT gene. This region is believed to be hTERT promoter. In particular, a 181 bp sequence located upstream of the translation initiation site is a core region important for the expression of the downstream gene. In the present invention, any sequence comprising this core region may be used. Preferably, an upstream sequence of approximately 378 bp containing the entire core region is used as hTERT promoter. It has been confirmed that this sequence of approximately 378 bp is equivalent to the 181 bp core region alone in gene expression efficiency. The nucleotide sequence of hTERT is shown in SEQ ID NO: 1.

The reason why an E1A gene, an IRES sequence and an E1B gene are located in this order in the present invention is that insertion of the IRES sequence between the E1A gene and E1B gene will results in higher replication ability of the virus when a host cell has been infected with it. E1A gene and E1B gene are genes included in E1 gene. This is one of early genes of viruses, which have early (E) genes and late (L) genes involved in their DNA replication, and encodes a protein involved in the regulation of transcription of viral genome. E1A protein encoded by E1A gene activates the transcription of a group of genes (E1B, E2, E4, etc.) necessary for the production of infectious virus. E1B protein encoded by E1B gene assists the accumulation of late gene (L gene) mRNA in the cytoplasm of the infected host cell to thereby inhibit the protein synthesis in the host cell. Thus, E1B protein promotes viral replication. The nucleotide sequences of E1A gene and E1B gene are shown in SEQ ID NO: 2 and SEQ ID NO: 3, respectively.

IRES (Internal Ribosome Entry Site) is a protein synthesis initiation signal specific to picornavirus. It is believed that this site serves as a ribosome-binding site because it has a complementary sequence to the 3' terminal sequence of 18S ribosomal RNA. It is known that mRNA derived from a virus which belongs to picornaviridae is translated via this sequence. Translation efficiency from IRES sequence is high. Even from the middle of mRNA, protein synthesis is performed in a cap structure non-dependent manner. Therefore, in the virus of the present invention, both E1A gene and E1B gene (which is located downstream of the IRES sequence) are translated independently by a human telomerase promoter. By using IRES, the control of expression by a telomerase promoter is exerted on E1A gene and E1B gene independently. Therefore, compared to cases where either E1A gene or E1B gene is controlled by a telomerase promoter, viral replication can be more strictly limited to those cells having telomerase activity. IRES sequence is shown in SEQ ID NO: 4.

In the present invention, a promoter from human telomerase is located upstream of the E1 gene because such a promoter is capable of promoting the replication in cells having telomerase activity.

The genes contained in the replication cassette of the present invention may be obtained by conventional genetic engineering techniques. Hereinbelow, it will be described taking an example where hTERT is used as human telomerase.

E1A gene and E1B gene may be amplified in E1 gene-expressing cells, such as 293 cells, by carrying out RT-PCR and/or DNA-PCR using primers such as E1A-S, E1A-AS, E1B-S and E1B-AS. If necessary, their sequences are confirmed using a known method such as TA cloning. Then, DNA fragments of E1A and E1B may be cut out using a known restriction enzyme.

Subsequently, E1A-IRES-E1B may be inserted into a known vector (such as pIRES) and then hTERT promoter sequence cut out with restriction enzymes (such as MluI, BglIII) may be inserted upstream of E1A.

If necessary, cytomegalovirus (CMV) promoter contained in a known vector, such as pShuttle, may be removed with restriction enzymes, such as MfeI and NheI; then, a sequence which is cut out from phTERT-E1A-IRES-E1B with restriction enzymes NheI and NotI may be inserted into that site. The adenovirus used in the present invention where a replication cassette consisting of hTERT-E1A-IRES-E1B is integrated is designated "Telomelysin".

In the recombinant virus used as a reagent of the present invention, a labeling cassette is also included together with the replication cassette. The "labeling cassette" is integrated in E3 region of the viral genome.

Here, it should be noted that the primary function of the virus vector used in the present invention is cytotoxicity by viral replication. Therefore, in order to use the reagent of the present invention for the purpose of diagnosing microcancer tissues, occurrence of the cytotoxicity is preferably as late as possible. This is because the expression of fluorescence caused by the replication of the recombinant virus of the present invention disappears when cells are destroyed, and it becomes difficult to identify the site of the microcancer tissue.

On the other hand, E3A and E3B exist in E3 region of adenovirus, and 11.6 kDa ADP (adenovirus death protein) in E3A region has a function to promote cytotoxicity and viral dispersion.

Therefore, the ADP-containing E3 region is removed from the recombinant virus used in the present invention to thereby delay the timing of cell death, which makes it easy to identify cancer tissues by the expression of fluorescence such as GFP.

The labeling protein which constitutes the labeling cassette is a protein which emits light in those cells where the above-described virus has replicated, and is visualized. Preferably, a substance which emits fluorescence is used. Examples of such substances include, but are not limited to, green fluorescent protein (GFP) derived from luminescent jellyfish such as *Aequorea victoria*, enhanced-humanized GFP (EGFP) or red-shift GFP (rsGFP) which are modified variants of GFP (GFP variants). It is also possible to use yellow fluorescent protein (YFP), cyan fluorescent protein (CFP), blue fluorescent protein (BFP), or *Renilla reniformis*-derived GFP. A gene encoding any of these proteins may be used in the present invention.

Examples of promoters capable of regulating the expression of the above-described gene include, but are not limited to, SV40 late promoter, MMTV LTR promoter, RSV LTR promoter, and SRα promoter. Preferably, cytomegalovirus (CMV) promoter may be used.

The recombinant gene contained in the labeling cassette of the present invention may be obtained by conventional genetic engineering techniques. For example, the recombinant gene may be prepared by inserting CMV-EGFP-SV40P (A) from pEGFP-N1 (CLONTECH) into shuttle plasmid pHM11, and inserting Csp45I fragment of this plasmid into ClaI site of pShuttle vector in which phTERT-E1A-IRES-E1B has been integrated.

Subsequently, a recombinant virus can be prepared by introducing the thus prepared gene comprising the replication cassette and the labeling cassette into a virus. For example, a sequence of a necessary region may be cut out with restriction enzymes from the recombinant gene as prepared above, and inserted into a viral DNA such as Adeno-X Viral DNA using a commercial kit such as Adeno-X Expression System (CLONTECH) (the resultant virus is designated "AdenoX-hAIB").

This AdenoX-hAIB is linearized with a known restriction enzyme, such as PacI, and then transfected into cultured cells, such as 293 cells, to thereby prepare an infectious recombinant virus.

The target cancer cells to be detected in the present invention are not limited. Cancer cells of any kind may be used. For example, solid cancers in the head and neck, stomach, large colon, lung, liver, prostate, pancreas, esophagus, bladder, gallbladder/bile duct, breast, uterus, thyroid, ovary, etc.; or leukemia, lymphoma, sarcoma, mesenchymal tumor or the like may be used. Most of cancer cells derived from human tissues show increase in telomerase activity. The present invention is capable of detecting those cancer cells in general where proliferation has been activated by such telomerase activity.

Since telomerase expression is extremely high in cancer cells compared to normal cells, hTERT is expressed in telomerase-containing cancer cells and the replication cassette functions therein. As a result, the virus replicates, which in turn increases the replication of the labeling protein. Thus, the labeling protein is expressed and visualized.

Therefore, when the reagent of the present invention does not emit fluorescence in normal cells, but whereas emits fluorescence in cancer cells. Thus, it is possible to observe cancer cells visually.

For the infection of cells with a recombinant virus, the following method may be used, for example. First, cells such as human large colon cancer cell SW620, human lung cancer cells A549 and H1299 are plated in culture plates containing an appropriate culture broth and cultured in the presence of $CO_2$ gas at 37° C. As the culture broth, one which is conventionally used for culturing animal cells may be used, e.g. DMEM, MEM, or RPMI-1640. If necessary, serum, antibiotics, vitamins, or the like may be added thereto. A specific amount (0.1-10 MOI (multiplicity of infection), preferably 1 MOI) of the recombinant virus of the present invention is inoculated into the cultured cells for infection. MOI means a ratio between the viral quantity (infective unit) and the number of cells when a specific amount of cultured cells are infected with a specific amount of viral particles. MOI is used as an indicator when cells are infected with virus.

In order to confirm viral replication, cells infected with virus are recovered and DNA is extracted therefrom. Then, the DNA is subjected to real time-PCR using primers targeting an appropriate gene contained by the virus of the present invention. Thus, quantitative analysis is possible.

With respect to the detection of labeled cells, cancer cells can be visualized because cells where viral replication is observed emit a specific fluorescence (e.g. green fluorescence when GFP is used) by exposing to excitation light. For example, when cells infected with virus are observed under fluorescence microscope, expression of GFP fluorescence in the cells can be observed. For the observation of infected cells with the passage of time, expression of GFP fluorescence may be observed with a CCD camera.

For the real time labeling and detection of cells of interest in vivo, the recombinant virus of the present invention may be administered into the living body.

The reagent of the present invention may be applied to the diseased site as it is. Alternatively, the reagent of the present invention may be introduced into the living body (target cell or organ) by any known method, e.g. intravenous, intramuscular, intra-abdominal or subcutaneous injection; inhalation through the nasal cavity, oral cavity or lung; oral administration; intravascular administration using catheter or the like. Dose levels are selected appropriately depending on the kind of active ingredient, the administration route, the target of administration, and the age, body weight, sex, symptoms and other conditions of the patient. Usually, dose levels may be selected so that the virus of the present invention (the active ingredient) is administered at a daily dose of about $10^6$-$10^{11}$ PFU (plaque forming units), preferably about $10^9$-$10^{11}$ PFU. This amount may be administered once a day, or may be divided into several portions and administered at several times a day.

The reagent of the present invention makes it possible to observe the label in vivo in real time. Thus, the reagent of the present invention is advantageous for use as an in vivo diagnosis agent. This is useful in the so-called navigation surgery.

If excision is performed in a wade range including the diseased organ in a surgical operation, the patient who survived this surgical operation can enjoy a long survival. However, the rate of occurrence of complications caused by the surgical operation itself becomes high. Further, loss of the function of the excised organ inevitably influences on the daily life after the surgical operation. It is important in cancer treatment to introduce a low-invasive treatment to reduce the burden of patients while maintaining the remote result of long survival.

When a low-invasive operation is pursued by minimizing the area of excision, one of the information pieces wanted is the presence or absence of metastatic lymph nodes. As a method for obtaining that information, sentinel node (SN) is attracting attention. SN is the lymph node which first receives the lymph flow from tumors, and there is a hypothesis that the first micro-metastasis occurs in this lymph node. This hypothesis is called the SN theory. Although large scale clinical tests in breast cancer have already been started in primarily Europe and the United States, whether or not this theory is applicable to other solid tumors is still unknown. Examination has just been started.

In vivo cancer diagnosis system using the reagent of the present invention is capable of establishing the technology of allowing direct expression of a fluorescent protein in cancer cells and identifying tumor tissues or metastasis-positive lymph nodes by a highly sensitive, fluorescence detection system during surgical operation. In other words, the technology of "navigation surgery" can be established as a method that is more effective than SN. The recombinant virus of the present invention replicates in a great number of cancer cells having telomerase activity, and those cells can emit, for example, a strong green fluorescence of GFP.

From the analysis of mono-lymph node metastasis sites, about 10% of skip metastasis, i.e., incipient metastasis to the second group or more remote lymph nodes skipping over the first group lymph nodes has been reported. Based on this report, there are a large number of researchers who have pointed out the danger of SN navigation. However, the in vivo cancer diagnosis system using the reagent of the present invention identifies tumor tissues or metastasis-positive lymph nodes directly during the surgical operation in real time and the excision range is navigated. This system is original and epoch-making, and further it is extremely practical for smooth progress of surgical operation. Specifically, the reagent of the present invention is endoscopically injected into the site of tumor (e.g., gastric or large colon mucosa around gastric cancer or large colon cancer; internal region of tumors such as gastric cancer, large colon cancer, lung cancer, pancreatic cancer) several days prior to the surgical operation with the same manual technique used in SN navigation. Then, sufficient time is provided so that the virus is distributed into tumor-infiltrated tissues, metastatic tumor tissues or attending lymph nodes to replicate in tumor sites or metastasis-positive sites.

At the time of surgery, excitation light for GFP fluorescence is projected from the light source onto the surgery field after ventrotomy, and images from a special 3CCD camera are projected on a face mount display. By using a transmissible lens, the visual field of the actual surgical field can also be secured, and it is possible to detect metastasis-positive lymph nodes from overlapped GFP images. Further, by mounting a special filter, it becomes possible to recognize fluorescence with the eyes without using the camera.

2. Reagent for Ex Vivo Diagnosis

The reagent of the present invention is also applicable to an ex vivo diagnosis agent for the purpose of screening. Currently, quantitative determination of tumor markers is the most common method to know the presence of cancer which cannot be detected with the eyes or its primary focus cannot be identified. However, tumor markers are not necessarily satisfactory in their cancer specificity. Besides, it is extremely difficult to detect every cancer species with a single marker.

It has been confirmed that telomerase activity increases in 85% or more of human malignant tumors, and thus its cancer specificity is believed to be extremely high.

Ex vivo cancer diagnosis using the reagent of the present invention may be performed, for example, as described below.

Erythrocytes are removed from a total blood sample taken from a subject. To the remaining cell suspension liquid, the reagent of the present invention is added at a specific ratio (0.1-10 MOI, preferably 1 MOI) and mixed in a test tube. The mixture is left for a specific period of time (e.g., 12-48 hr) to promote infection of cancer cells with the virus and the resultant viral replication. Then, the GFP expression in the cell fraction is analyzed quantitatively by flow cytometry. With the use of this system, it becomes possible to detect free cancer cells present in the peripheral blood with high sensitivity. This method can be used for detecting free cancer cells present in the peripheral blood only in an extremely small quantity.

3. Cell Death-Inducing Agent and Method of Inducing Cell Death

The present invention provides a cell death-inducing agent, comprising a recombinant virus where a replication cassette comprising a promoter from human telomerase, an E1A gene, an IRES sequence and an E1B gene in this order is integrated in E1 region of the viral genome and a cell death-inducing cassette comprising a gene encoding a protein associated with cell death induction and a promoter capable of regulating the expression of the gene encoding the protein is integrated in E3 region of the viral genome. Preferably, the cell death-inducing agent of the present invention is used in gene therapy for cancers as an agent for inducing cell death in cancer cells, and may also be used for prevention of recurrence, inhibition and/or prevention of metastasis after surgical operation of cancers.

In the cell death-inducing cassette of the recombinant virus contained in the cell death-inducing agent of the present invention, a gene is integrated which is operated by a promoter and encodes a protein capable of inducing cell death.

In this cell death-inducing cassette used in the recombinant virus, a gene encoding a protein associated with cell death induction and a promoter capable of regulating the expression of the gene are contained. Therefore, when the cell death-inducing agent of the present invention is introduced into cancer cells, the virus replicates specifically in the cancer cells. As a result, intracellular expression level of the cell death-inducing protein increases, enabling induction of cell death only in the cancer cells without damaging normal cells.

A gene encoding a protein associated with cell death induction refers to a gene encoding a protein associated with the induction of cell death in a specific cell.

Specific examples of proteins associated with cell death induction include the following proteins, but are not limited to them. In the present invention, a gene encoding any of these proteins may be integrated.

As a specific example of immunity-associated protein, PA28 may be given. PA28 is a protein which activates intracellular proteasomes. When overexpressed, this protein causes immunological reactions and at the same time induces cell death. As a specific example of apoptosis-inducing protein, TRAIL may be given. TRAIL is a molecule which induces apoptotic cell death by binding to the receptor on cell surfaces. As a specific example of telomerase-associated protein, AU5 may be given. AU5 has a sequence capable of inducing cell death in cells having telomerase activity.

The genes for these proteins associated with cell death induction may be obtained as described below.

Briefly, primers specific for each gene are designed and the gene sequence is amplified with PCR equipment. Then, DNA sequencing is carried out to confirm that the expected gene has been obtained.

Antioncogenes are also included in cell death-inducing substances for cancer cells, because antioncogenes have a function of inhibiting the replication of cancer cells. For this purpose, the following antioncogenes used in conventional gene therapy may be enumerated.

p53, p14, p16: various kinds of cancers
APC: large colon cancer, gastric cancer, pancreatic cancer
BRCA-1: ovary cancer, breast cancer
DPC-4: large colon cancer, pancreatic cancer
FHIT: gastric cancer, lung cancer, uterus cancer
p73: neuroblastoma
Patcded: basal cell carcinoma
Rb: lung cancer, osteosarcoma
DCC: large colon cancer
NF1: neurofibromatosis type 1
NF2: neurofibromatosis type 2
WT-1: Wilms' tumor As a promoter capable of regulating the expression of the above gene, a cytomegalovirus (CMV) promoter may be used preferably. Other promoters such as SV40 late promoter, MMTV LTR promoter, RSV LTR promoter, and SRα promoter may also be used.

The cell death-inducing agent of the present invention may be applied to the diseased site as it is. Alternatively, the agent of the present invention may be introduced into the living body (target cell or organ) by any known method, e.g. intravenous, intramuscular, intra-abdominal or subcutaneous injection; inhalation through the nasal cavity, oral cavity or lung; oral administration; intravascular administration using catheter or the like.

The cell death-inducing agent of the present invention may be treated, for example, by the method such as freezing to enable easy handling and then used alone, or prepared into pharmaceutical compositions by mixing with known pharmaceutically acceptable carriers such as excipients, fillers, binders, lubricants; or known additives (including such as buffers, isotonic agents, chelating agents, coloring agents, preservatives, flagrances, flavoring agents, and sweetening agents).

The cell death-inducing agent of the present invention may be administered orally or parenterally depending on the form of the agent, e.g. oral administration agents such as tablets, capsules, powders, granules, pills, liquids, syrups, etc. and parenteral administration agents such as injections, external medicines, suppositories, eye drops, etc. Preferably, local injection into muscle or abdominal cavity, or intravenous injection may be enumerated.

Dose levels are selected appropriately depending on the kind of active ingredient, the administration route, the target of administration, and the age, body weight, sex, symptoms and other conditions of the patient. Usually, dose levels may be selected so that the virus of the present invention (the active ingredient) is administered at a daily dose of about $10^6$-$10^{11}$ PFU (plaque forming units), preferably about $10^9$-$10^{11}$ PFU. This amount may be administered once a day, or may be divided into several portions and administered at several times a day.

When the virus of the present invention is administered, it is also possible to use a known immunosuppressant or the like to suppress the immunity of the living body to thereby make the viral infection easy.

Further, the virus of the present invention may be used jointly with at least one anticancer agent selected from the group consisting of known anticancer agents and radiation.

It is believed that there is an extremely low possibility that the cell death-inducing agent of the present invention will produce side effects for the reasons described below. Thus, the cell death-inducing agent of the present invention can be a very safe preparation.

(1) There is little telomerase activity in normal somatic cells, and yet the virus of the present invention is hard to be infectious in suspending cells such as hematopoietic cells.

(2) Since the virus of the present invention has replication ability, it is possible to use this virus at a lower concentration than that of conventional non-replication competent virus used in conventional gene therapy.

(3) Even when the virus of the present invention has been administered in excess, antiviral action works through ordinary immune reaction in the living body.

It is possible to induce cell death in a target cell by infecting the target cell with the recombinant virus of the present invention. The kinds of target cells are not particularly limited. For example, tumor cells, cells with active replication, cells whose telomerase activity has been increased, or the like may be used.

The expressing "infecting cells with the recombinant virus" means as described above. In order to confirm whether cell death has been induced or not, morphological observation may be performed as described below. Briefly, cells adhering to the bottom of a culture dish are infected with the recombinant virus of the present invention. After a specific time period, the form of the cells becomes circular and they suspend in the culture broth as glossy cells peeled off from the bottom. At this point, the life maintaining mechanism in these cells has been broken up, and it can be measured that cell death has been induced. Alternatively, it is also possible to confirm cell death with a commercial viable cell assay kit using tetrazorium salts (e.g., MTT, XTT).

Hereinbelow, the present invention will be described in more detail with reference to the following Examples. However, the present invention is not limited to these Examples.

Example 1

Visualization of Cancer Cells by In Vitro Co-Infection

This Example preliminary examined whether or not fluorescence will be emitted in vitro when cancer cells are co-infected with virus Telomelysin comprising the replication cassette and non-replicating virus Ad-GFP comprising the labeling cassette.

Figure 2:
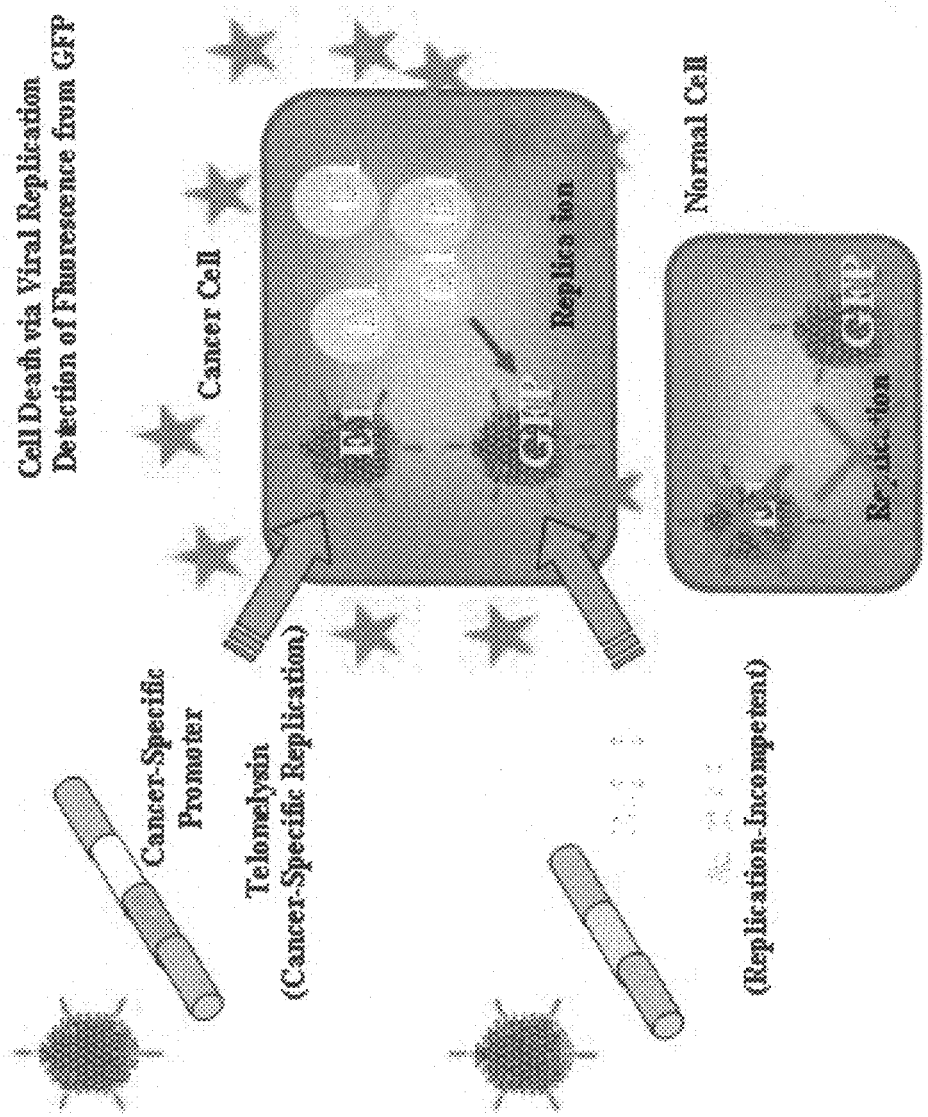
FIG. 2 is a diagram showing the replication of the non-replicating virus.

Human large colon cancer cell SW620 and human lung cancer cells A549 and H1299 were infected with 0.1 MOI (multiplicity of infection) of Ad-GFP (FIG. 2).

Figure 3:
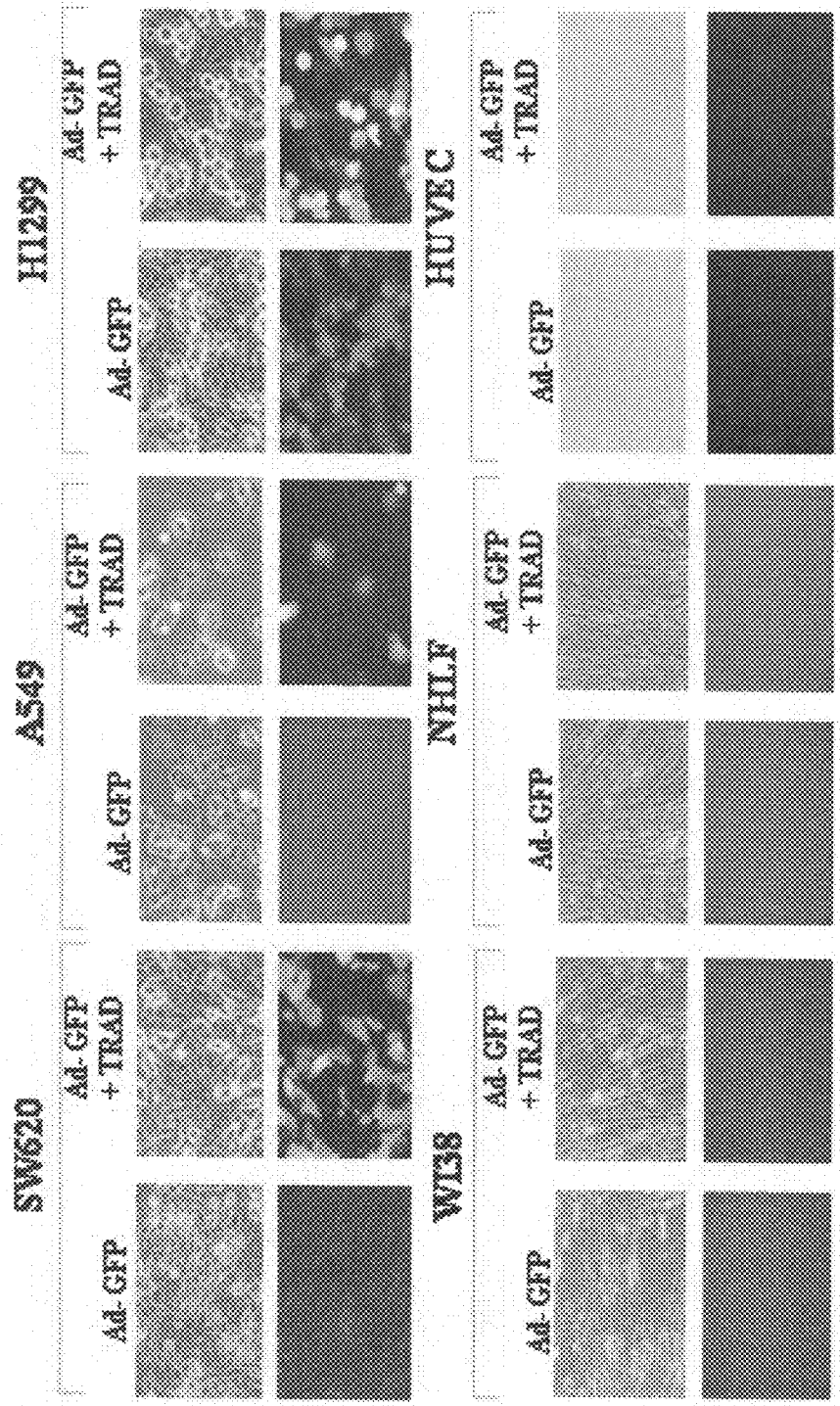
FIG. 3 is a diagram showing the results of detection of cancer cells by in vitro co-infection with Ad-GFP.

As a result, tendency to green color was hardly recognized when human large colon cancer cell SW620 and human lung cancer cells A549 and H1299 were infected with 0.1 MOI of Ad-GFP. However, when 1 MOI of TRAD was used jointly, fluorescence could be detected only in cancer cells, and no fluorescence was detected in normal cells such as human fibroblast cells WI38 and NHLF and human umbilical vascular endothelial cell (HUVEC) (FIG. 3).

Example 2

Visualization of Cancer Tissues by In Vivo Co-Infection with Telomelysin and Ad-GFP This Example preliminary examined whether or not fluorescence will be emitted in vivo when cancer tissues are co-infected with virus Telomelysin comprising the replication cassette and non-replicating virus Ad-GFP comprising the labeling cassette.

Ad-GFP ($8\times10^5$ PFU) and TRAD ($8\times10^6$ PFU) were intratumorally administered to human large colon cancer SW5620 and human lung cancer A549 tumors transplanted subcutaneously into the dorsal of nude mice. Then, fluorescence was observed with the passage of time.

Figure 4:
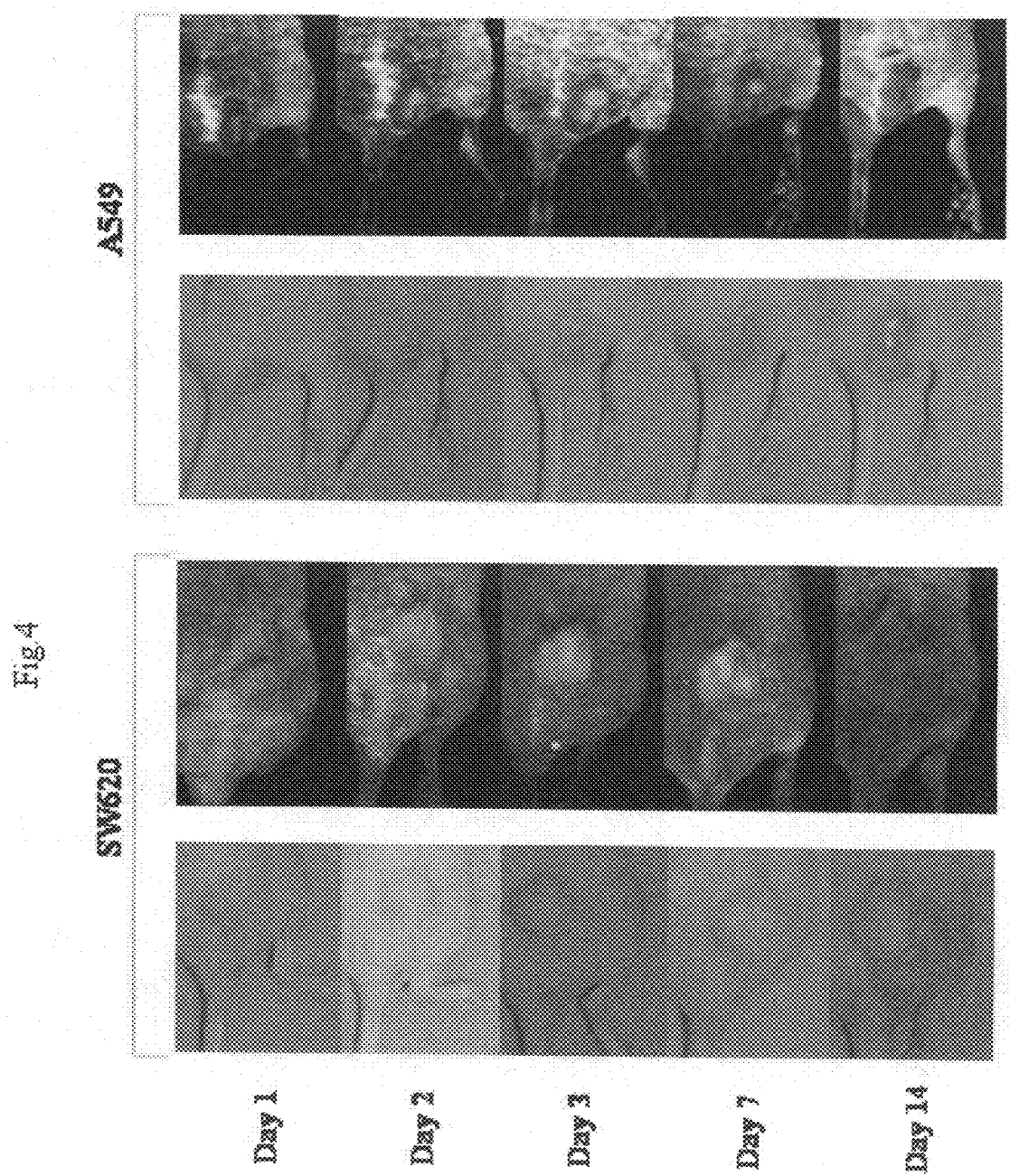
FIG. 4 is a diagram showing the results of detection of human cancer tissues by in vivo co-infection with Ad-GFP.

In any of the tumors, spot-like fluorescence had begun to be detected from day 2 after the administration and disappeared by day 14 (FIG. 4).

Example 3

Detection of Cancer Cells with Telomelysin-GFP

1. Preparation of GFP-Expressing, Replication-Competent Virus (Telomelysin-GFP) which Comprises the Replication Cassette Comprising Telomerase Promoter and E1 Gene and the Labeling Cassette Comprising Gene Encoding GFP in a Single Virus The outline of Telomelysin-GFP is shown in FIG. 1. Telomelysin-GFP proliferates/replicates cancer cell-specifically and telomerase-specifically because E1A/IRES/E1B is operated by the hTERT promoter. Further, Telomelysin-GFP also has an *Aequorea victoria*-derived GFP gene integrated in its E3 region which is operated by a promoter. Therefore, cells where viral replication is observed emit green fluorescence when excitation light is applied, which enables visualization of cancer cells.

Such a replication-incompetent virus was prepared as described below.

2. Preparation of Recombinant Virus

An E1A gene of 897 bp was amplified from RNA extracted from 293 cells by RT-PCR using the following specific primers (E1A-S and E1A-AS).

```
E1A-S:
5'-ACA CCG GGA CTG AAA ATG AG-3'    (SEQ ID NO: 5)

E1A-AS:
5'-CAC AGG TTT ACA CCT TAT GGC-3'   (SEQ ID NO: 6)
```

Composition of the PCR solution:
  1×PCR buffer
  0.2 mM each dNTPs
  5 mM $MgCl_2$
  2.5 U AmpliTaq Gold
  0.2 µM each Primers
Reaction conditions:
  95° C., 10 min
  (95° C., 1 min; 56° C., 1 min; 72° C., 1.5 min)×32 cycles
  72° C., 7 min
  4° C., 5 min An E1B gene of 1822 bp was amplified from DNA extracted from 293 cells by DNA-PCR using the following primers E1B-S and E1B-AS.

```
E1B-S:
5'-CTG ACC TCA TGG AGG CTT GG-3'    (SEQ ID NO: 7)

E1B-AS:
5'-GCC CAC ACA TTT CAG TAC CTC-3'   (SEQ ID NO: 8)
```

The composition of the PCR solution and the reaction conditions used were the same as used for the amplification of E1A gene.

Each PCR product was subjected to TA cloning (TA Cloning Kit Dual Promoter; Invitrogen) to thereby confirm their sequences. Then, DNA fragments of 911 bp (E1A) and 1836 bp (E1B) were cut out, respectively, with restriction enzyme EcoRI.

E1A and E1B were inserted into the MluI site and the SalI site, respectively, of pIRES vector (CLONTECH) in the normal orientation (E1A-IRES-E1B).

A 455 bp hTERT promoter sequence which had been cut out with restriction enzymes MluI and BglII was inserted into the XhoI site located upstream of the E1A of E1A-IRES-E1B in the normal orientation (phTERT-E1A-IRES-E1B).

The cytomegalovirus (CMV) promoter contained in pShuttle vector was removed by treatment with restriction enzymes MfeI and NheI. Then, a 3828 bp sequence cut out from phTERT-E1A-IRES-E1B using restriction enzymes NheI and NotI was inserted into that site (pSh-hAIB).

pEGFP-N1 (CLONTECH) was digested with AgeI/NheI, blunt-ended with Klenow fragment and self-ligated (pGFP-N2).

This pEGFP-N2 was digested with NsiI/AflII and blunt-ended with T4 DNA polymerase, followed by preparation of a BglII site using BglII linker. This BglII fragment was inserted at the BamHI site of pHM11 (pHM11-EGFP-N2).

Further, Csp45I fragment from pHM11-EGFP-N2 was inserted at the ClaI site of pShuttle vector in which phTERT-E1A-IRES-E1B had been integrated (pSh-hAIB).

A 4381 bp sequence was cut out from the thus prepared recombinant gene (pSh-hAIB) using restriction enzymes I-CeuI and PI-SceI, and inserted into the Adeno-X Viral DNA of Adeno-X Expression System (CLONTECH) (AdenoX-hAIB). This AdenoX-hAIB was treated with restriction enzyme PacI for linearization and then transfected into 293 cells to thereby prepare an infectious recombinant adenovirus (hereinafter, referred to as "Telomelysin-GFP").

Example 4

Detection Test on Human Lung Cancer Cells

1. Morphological Changes in Human Lung Cancer Cells Caused by Infection with Telomelysin-GFP Human non-small-cell lung cancer-derived H1299 cells cultured in vitro were infected with Telomelysin-GFP at 1 MOI or 10 MOI. Specifically, H1299 cells were plated in 24-well plates at $5 \times 10^4$ cells/well. After 24 hours, cells were counted and the virus was added to the culture broth to give a concentration of 1 MOI or 10 MOI. Subsequently, the morphology of cells was observed under inversed microscope with the passage of time to examine the cytotoxic activity of the virus.

Figure 5:
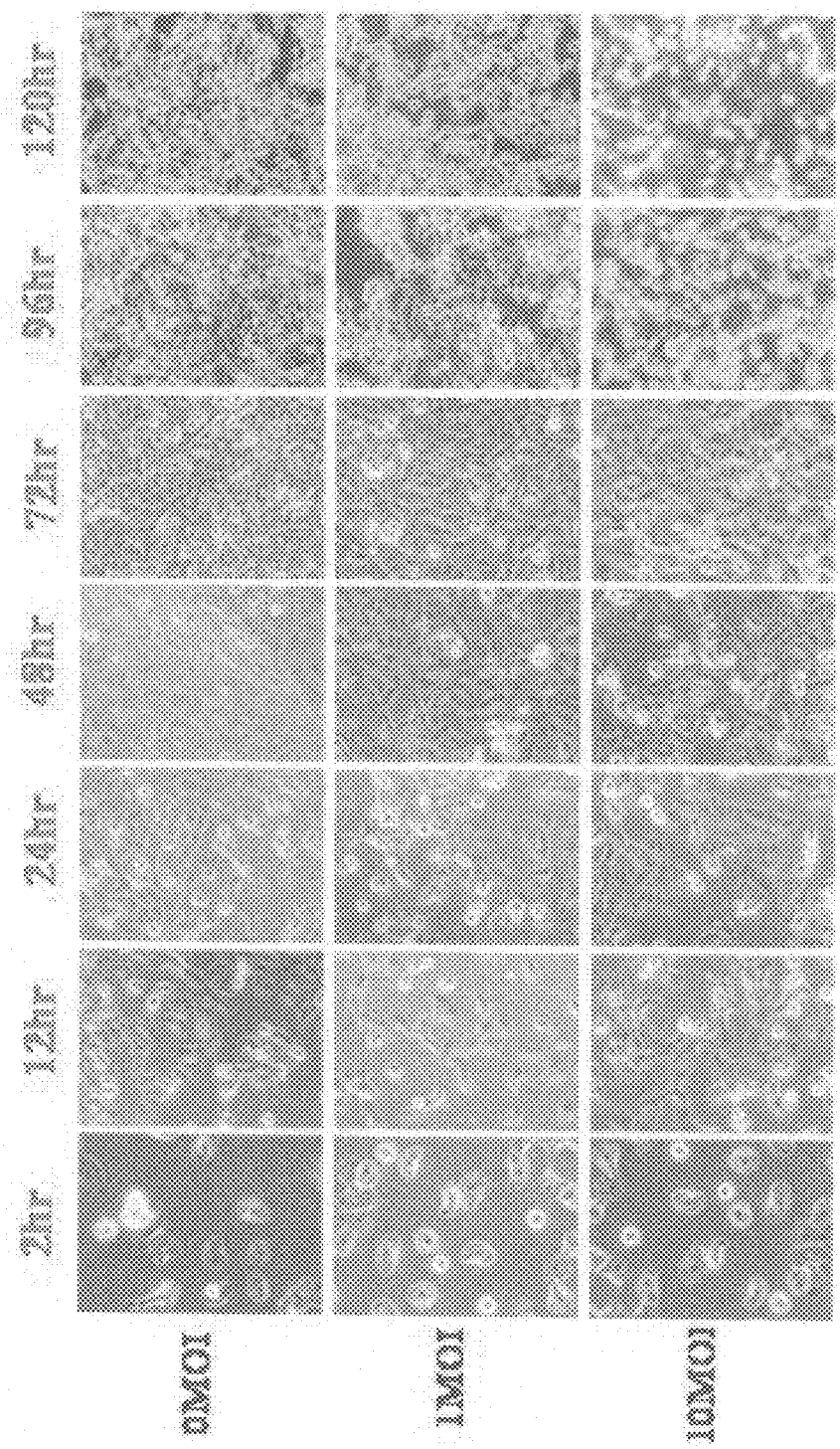
FIG. 5 is a diagram showing the morphological changes in human lung cancer cells infected with Telomelysin-GFP.

As a result, cell death was induced by viral replication in a concentration dependent manner and also a time dependent manner. 120 hours after 10 MOI infection, most of the cells became circular and were suspending under inverted microscope (FIG. 5).

Figure 6:
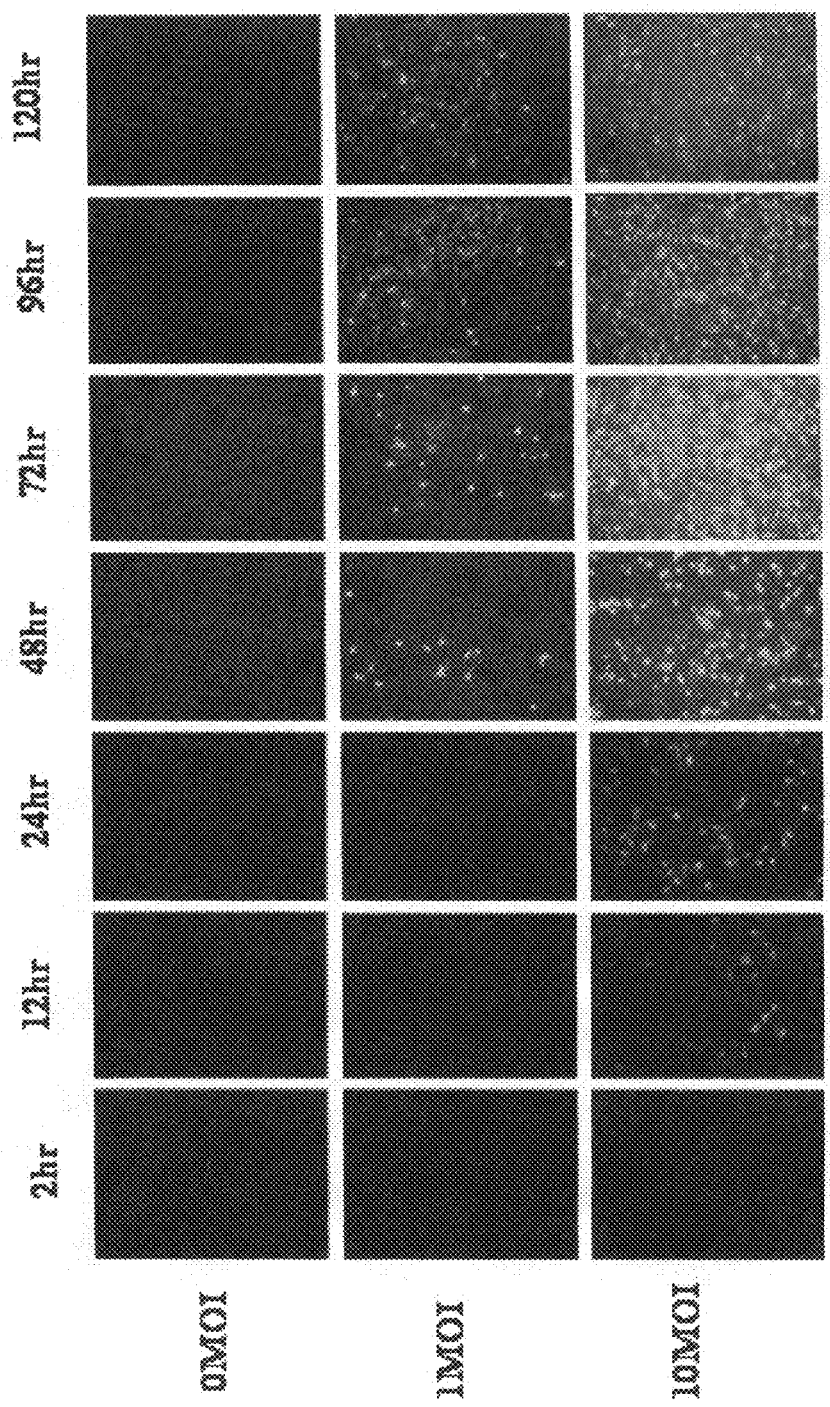
FIG. 6 is a diagram showing the expression of GFP fluorescence in human lung cancer cells infected with Telomelysin-GFP.

2. Expression of GFP Fluorescence in Human Lung Cancer Cells Caused by Infection with Telomelysin-GFP The inverted microscopic images shown in FIG. 6 were observed under fluorescent microscope. The green fluorescence of GFP indicating viral replication in a concentration dependent manner and also a time dependent manner was observed (FIG. 6). 72 hours after 10 MOI infection, GFP expression was observed in the maximum number of cells. Then, the number of GFP-positive cells decreased as cell death was induced (FIG. 6).

3. Verification of Telomelysin-GFP Replication by Quantitative Real Time PCR

Human lung cancer cell H1299 was infected with Telomelysin-GFP at 10 MOI. Cell samples were harvested at 2, 26, 50 and 74 hours after the infection and DNA was extracted therefrom. Real time PCR was performed using the following primers targeting the E1A gene of Telomelysin-GFP, to thereby quantitatively analyze the viral proliferation/replication.

```
E1A-S:
5'-CCT GTG TCT AGA GAA TGC AA-3'    (SEQ ID NO: 9)

E1A-AS:
5'-ACA GCT CAA GTC CAA AGG TT-3'    (SEQ ID NO: 10)
```

Figure 7:
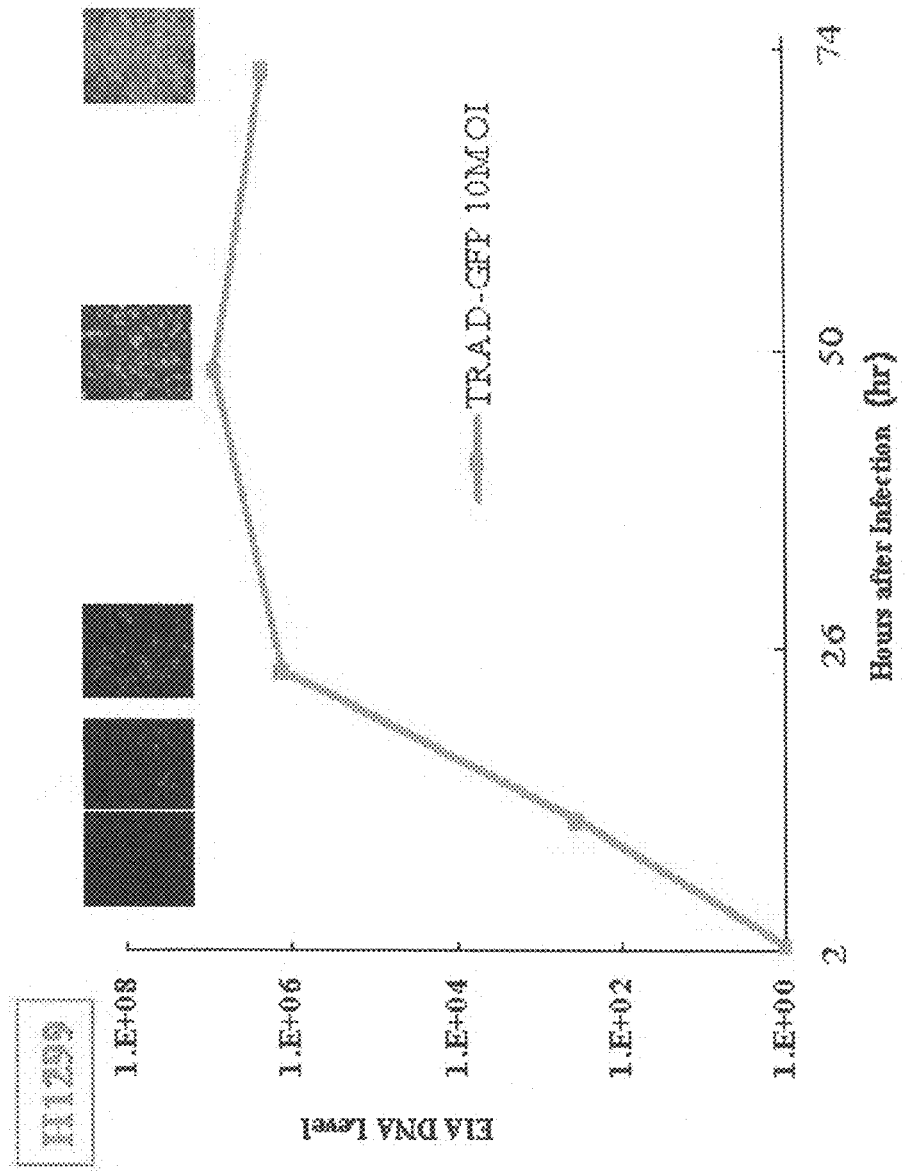
FIG. 7 is a diagram showing the replication of Telomelysin-GFP determined by quantitative real time-PCR.

Composition of PCR Solution:
  1× LC FastStart DNA Master SYBR Green I
  3 mM $MgCl_2$
  0.5 µM each Primer
Reaction Conditions:
  95° C., 10 min
  (95° C., 10 sec; 60° C., 15 sec; 72° C., 8 sec)×40 cycles
  70° C., 15 sec
  40° C., 30 sec The results revealed that Telomelysin-GFP had already replicated 1,000,000-fold at 26 hours after the infection (FIG. 7). Thereafter, the replication reached plateau, but GFP fluorescence was also enhanced gradually slightly after the replication (FIG. 7).

Example 5

Detection Test on Human Large Bowel Cancer Cells

1. Expression of GFP Fluorescence in Human Large Bowel Cancer Cells Caused by Infection with Telomelysin-GFP Human large colon cancer-derived SW620 cells were infected with Telomelysin-GFP. Changes in the cells were observed with the passage of time under inverted microscope and fluorescent microscope.

Figure 8:
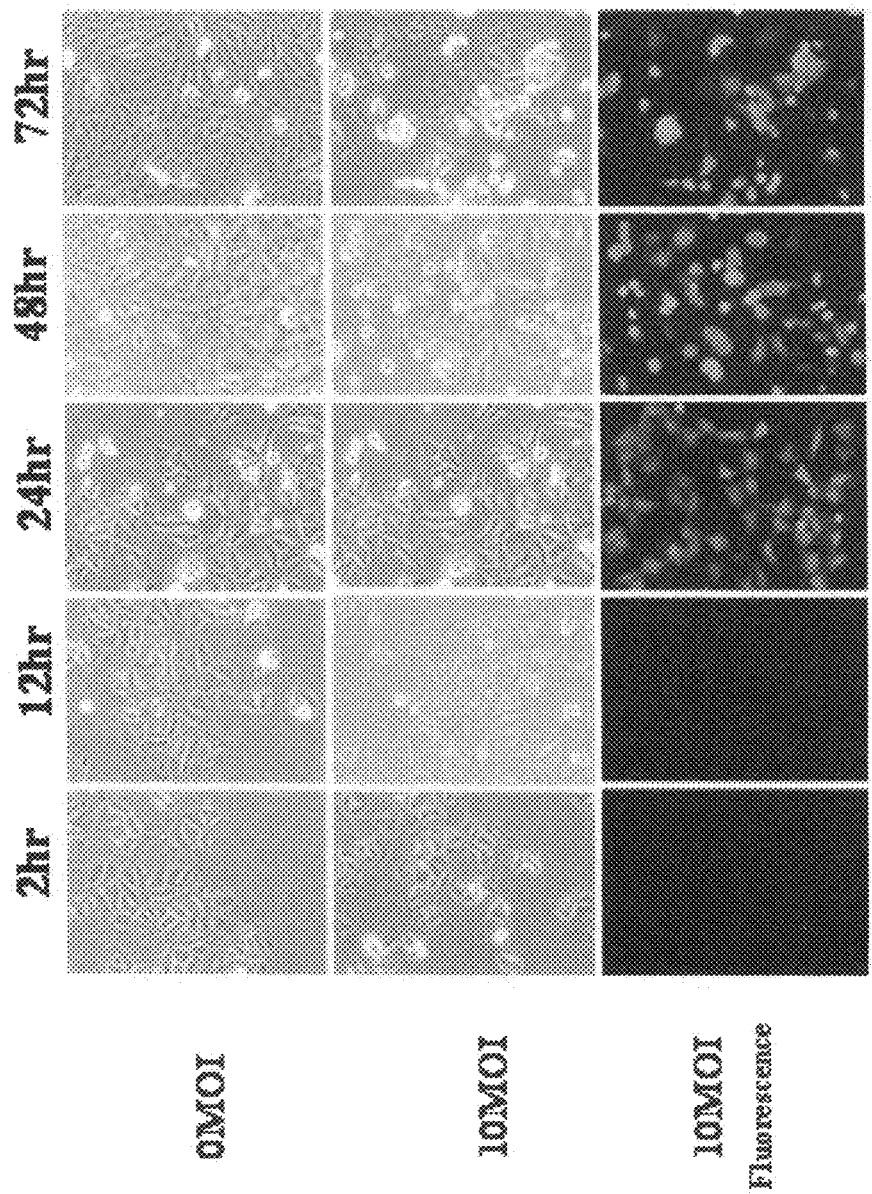
FIG. 8 is a diagram showing the expression of GFP fluorescence in human large colon cancer cells infected with Telomelysin-GFP.

As a result, GFP green fluorescence indicating viral replication in a time dependent manner was recognized as in the case of H1299 cells (FIG. 8).

2. Verification of Telomelysin-GFP Replication by Quantitative Real Time PCR

In the same manner as in H1299 cells, SW620 human large colon cancer cells were infected with Telomelysin-GFP at 10 MOI. Cell samples were harvested at 2, 26, 50, 74 and 98 hours after the infection and DNA was extracted therefrom. Real time PCR was performed using the following primers targeting the E1A gene of Telomelysin-GFP, to thereby quantitatively analyze the viral replication. Conditions of the real time PCR (composition of the reaction solution, cycle, time period, etc.) were the same as in H1299 cells.

Figure 9:
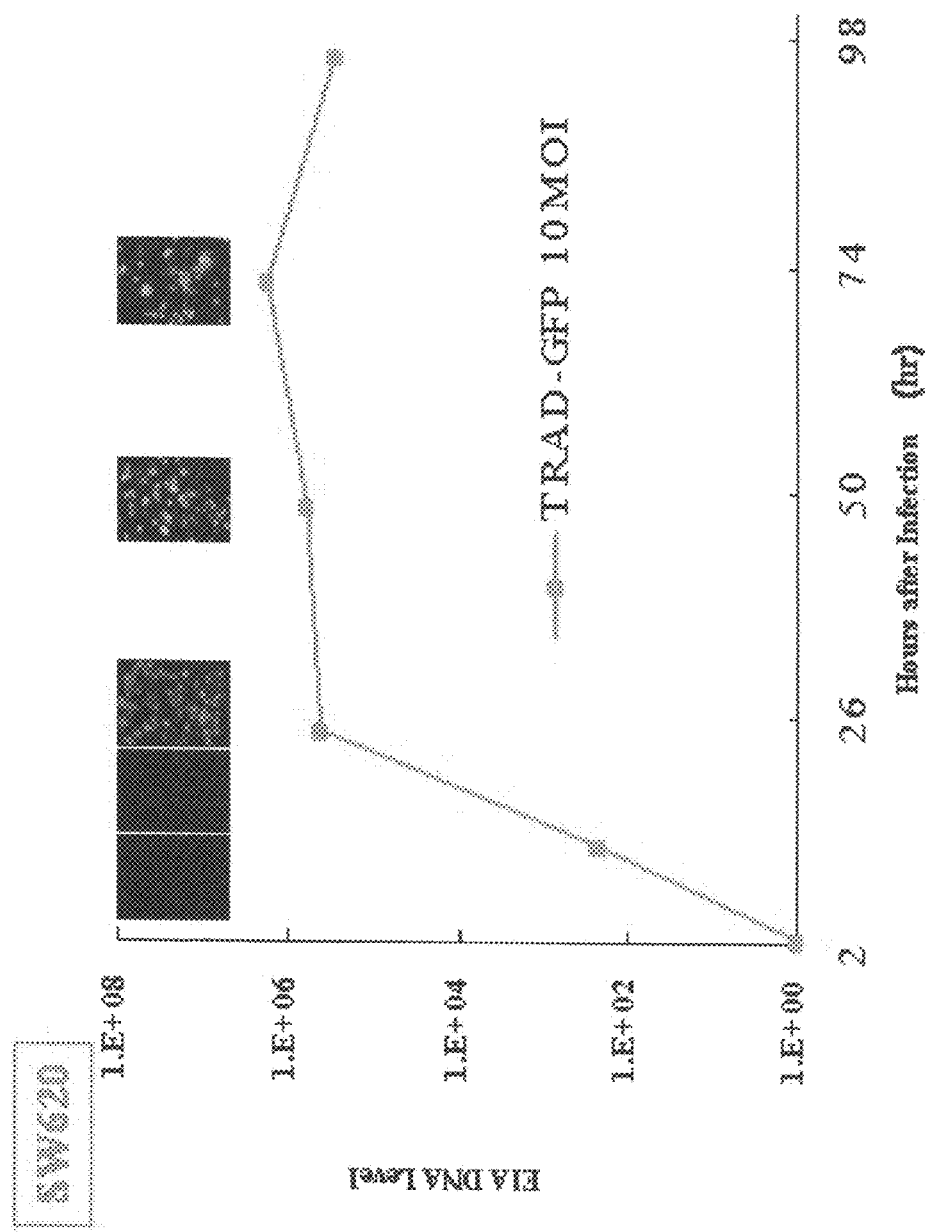
FIG. 9 is a diagram showing the replication of Telomelysin-GFP determined by quantitative real time-PCR.

The results revealed that Telomelysin-GFP had already replicated 1,000,000-fold at 26 hours after the infection and was almost plateau up to 98 hours after the infection (FIG. 9).

Example 6

1. Morphological Changes in Human Normal Lung Fibroblast Cells (NHLF) Caused by Infection with Telomelysin-GFP Normal human lung fibroblast cells (NHLF) cultured in vitro were infected with Telomelysin-GFP at 1 MOI or 10 MOI. Changes were observed under inverted microscope up to 120 hours after the infection.

Figure 10:
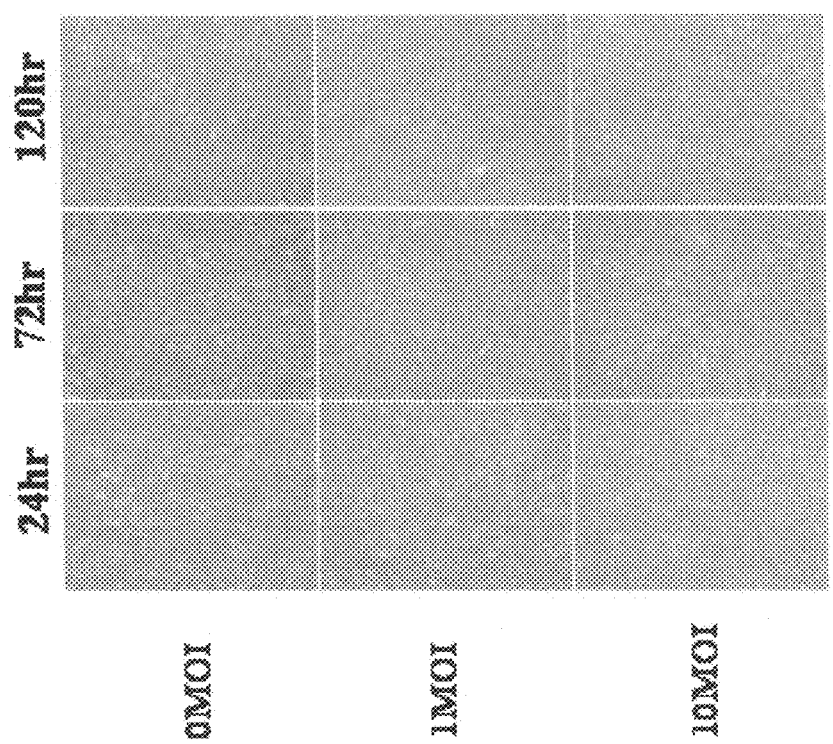
FIG. 10 is a diagram showing the morphological changes in normal human lung fibroblast cells (NHLF) infected with Telomelysin-GFP.

As a result, no morphological changes were observed, and cell death was not induced (FIG. 10).

Figure 11:
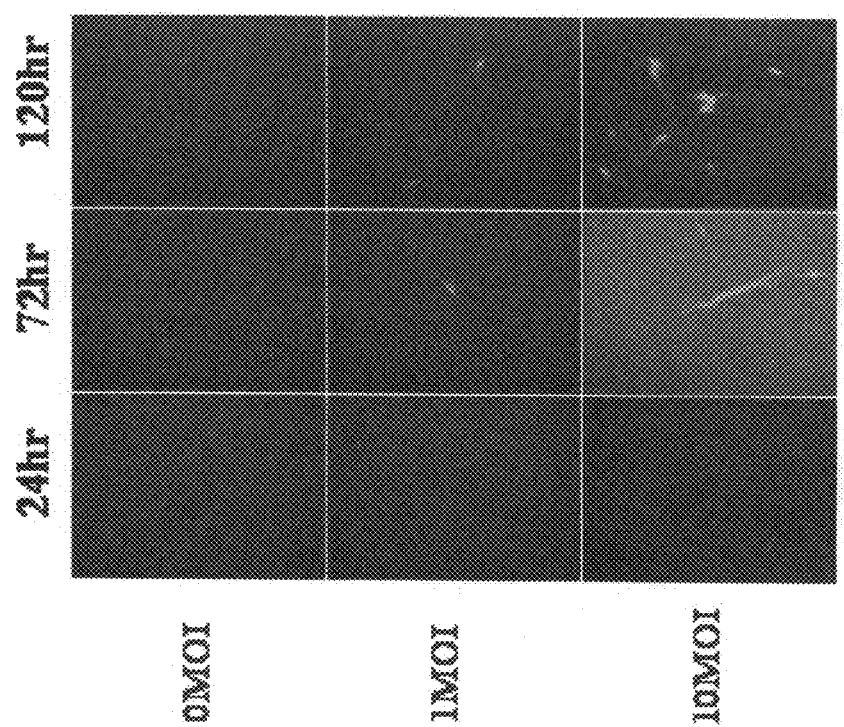
FIG. 11 is a diagram showing the expression of GFP fluorescence in normal human lung fibroblast cells (NHLF) infected with Telomelysin-GFP.

2. Expression of GFP Fluorescence in Normal Human Lung Fibroblast Cells Caused by Infection with Telomelysin-GFP When the inverted microscopic images shown in FIG. 10 are observed under fluorescent microscope, expression of GFP fluorescence was observed in some cells. However, considering the cell density, the expression was extremely rare compared to that in cancer cells. Therefore, it was believed that Telomelysin-GFP hardly proliferates/replicates in normal cells (FIG. 11).

3. Verification of Telomelysin-GFP Replication by
Quantitative Real Time PCR

H1299 human lung cancer cell, SW620 human large colon cancer cell, and normal human lung fibroblast cell (NHLF) were infected with Telomelysin-GFP at 10 MOI as described above. Cell samples were harvested with passage of time, and DNA was extracted therefrom. Then, viral replication was quantitatively analyzed by real time PCR.

Figure 12:
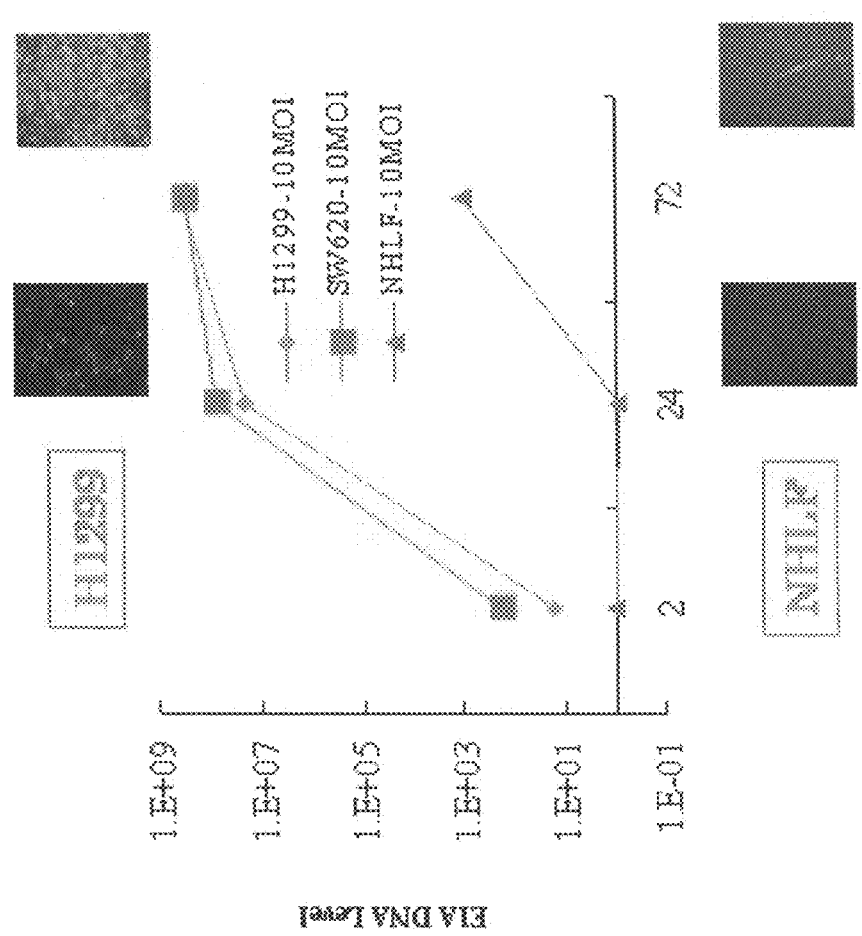
FIG. 12 is a diagram showing comparison of Telomelysin-GFP replications determined by quantitative real time-PCR.

The results revealed that Telomelysin-GFP had already replicated about 1,000,000-fold in cancer cells at 24 hours after the infection, and emitted remarkable GFP fluorescence at 72 hours after the infection (FIG. 12). On the other hand, replication was only about 1000-fold in NHLF cells even at 72 hours after the infection, and little GFP fluorescence could be detected (FIG. 12).

Example 7

Detection of Intratumoral Proliferation/Replication of Telomelysin-GFP by Fluorescence Imaging 1. Telomelysin-GFP (107 PFU) was administered into the tumor of H1299 human lung cancer transplanted into nude mice. Then, expression of GFP fluorescence was observed with a CCD camera with the passage of time.

Figure 13:
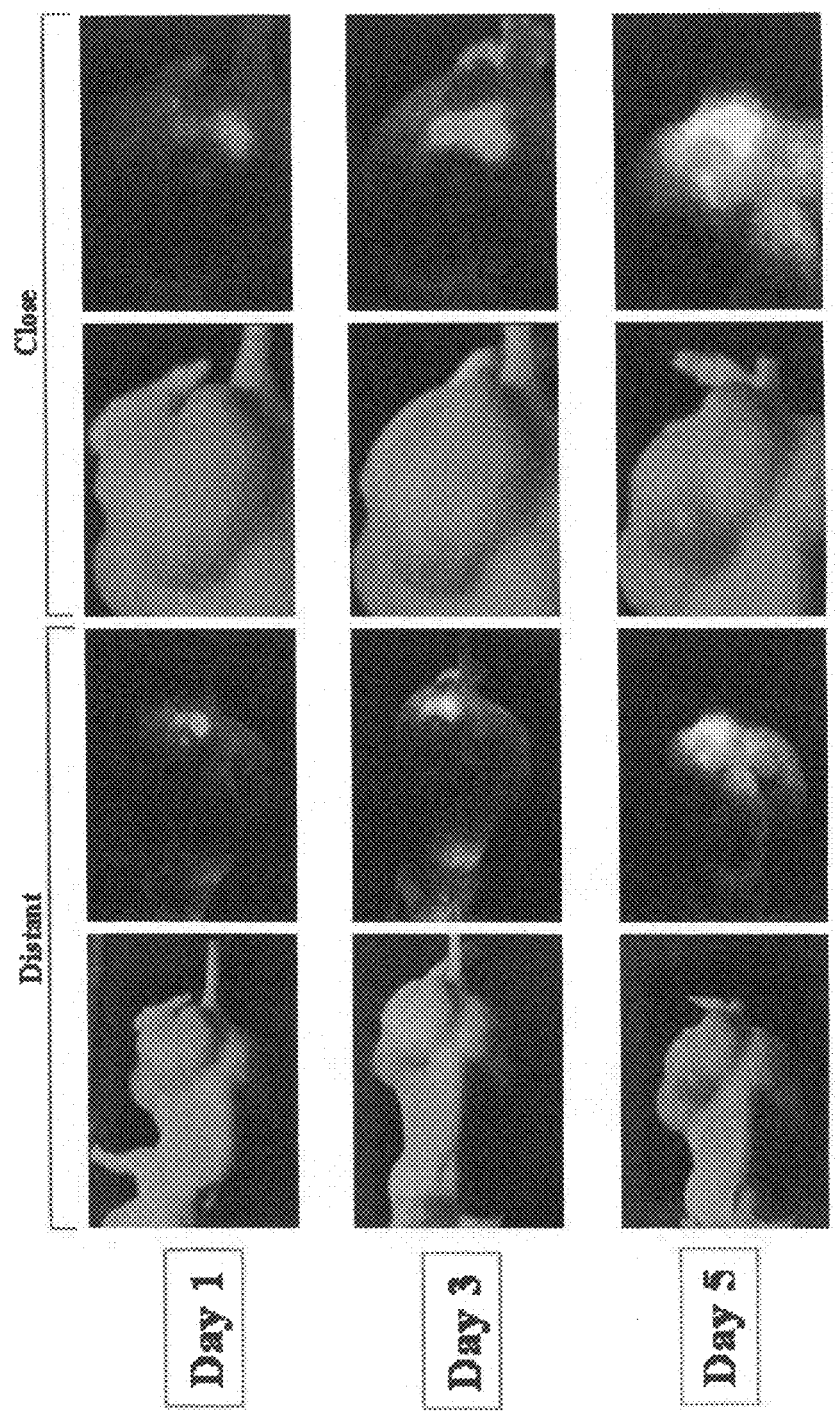
FIG. 13 is a diagram showing the intratumoral proliferation/replication of Telomelysin-GFP observed by fluorescence imaging.

The results revealed that expression of GFP fluorescence began to be recognized within 24 hours after the infection, and that the range and luminance were gradually enhanced 3 days and 5 days after the infection (FIG. 13).

2. In the same manner as described above, Telomelysin-GFP (107 PFU) was administered into the tumor of H1299 human lung cancer transplanted into nude mice. One week and three weeks after the infection, subcutaneous tumor was removed. Expression of GFP fluorescence was observed on the entire tumor and on a cut surface using a CCD camera.

Figure 14:
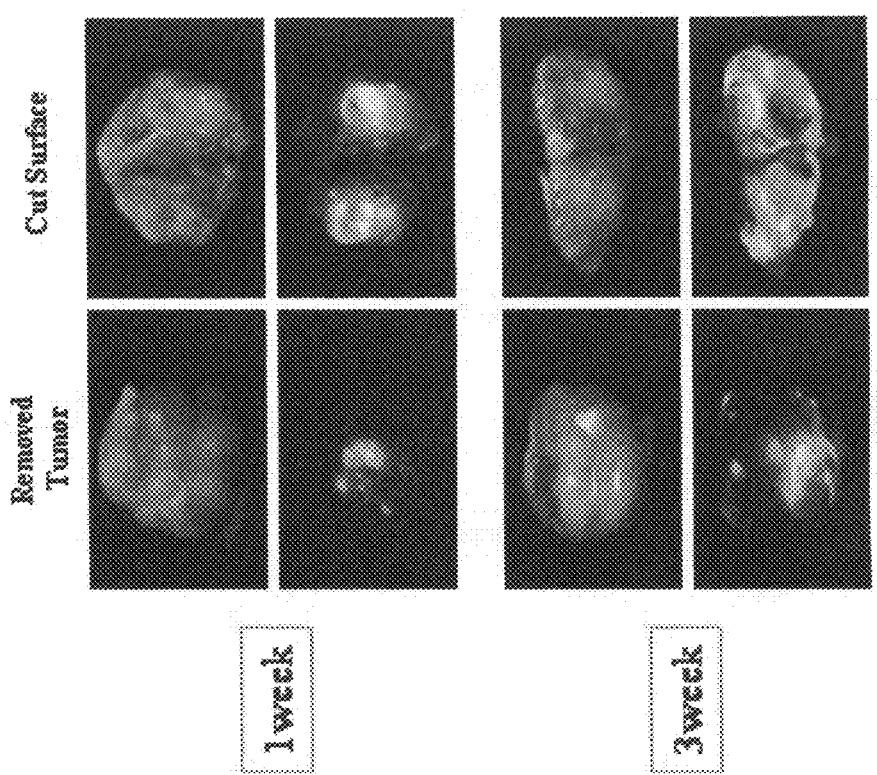
FIG. 14 is a diagram showing the intratumoral proliferation/replication of Telomelysin-GFP observed by fluorescence imaging.

As a result, even when fluorescence expression was weak on the surface of the removed tumor, replication of Telomelysin-GFP could be confirmed in a wide range on the cut surface (FIG. 14). In tissues three weeks after the infection fluorescence was recognized on almost all over the tumor (FIG. 14).

Figure 15:
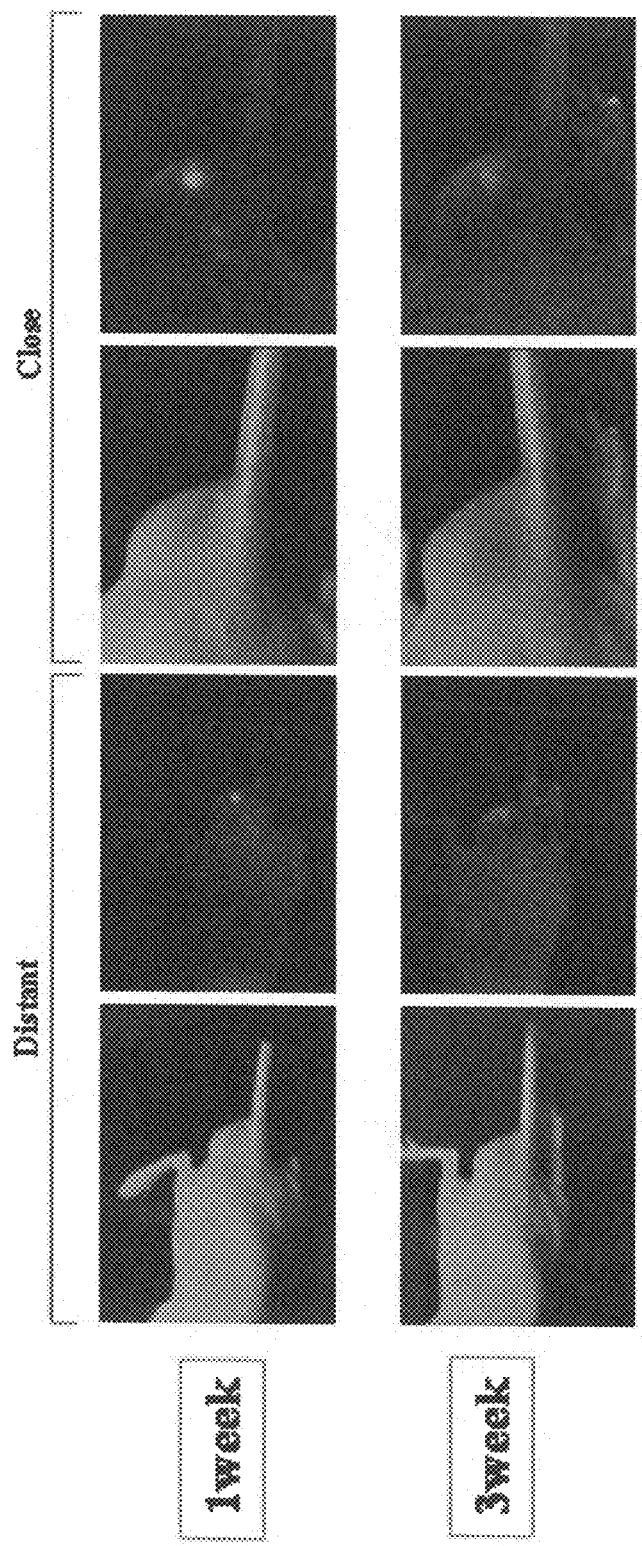
FIG. 15 is a diagram showing the intratumoral proliferation/replication of Telomelysin-GFP in a lymph node metastasis model observed by fluorescence imaging.

3. In the same manner as described above, HT29 human large colon cancer cell was transplanted into the rectal wall of nude mice as an orthotopic model, and Telomelysin-GFP (107 PFU) was administered at the time when gross tumor was formed. Expression of GFP fluorescence caused by Telomelysin-GFP replication began to be recognized one week after the infection with a CCD camera (FIG. 15). The fluorescence expression was maintained even three weeks after the infection (FIG. 15).

Example 8

1. Histological Analysis of Orthotopic Rectal Cancer Model Using Nude Mouse and HT29 Human Large Bowel Cancer Cell HT29 human large colon cancer cell was transplanted into the rectal wall of nude mouse. When gross tumor was formed, the tumor was removed and analyzed after hematoxylin-eosin (HE) staining.

Figure 16:
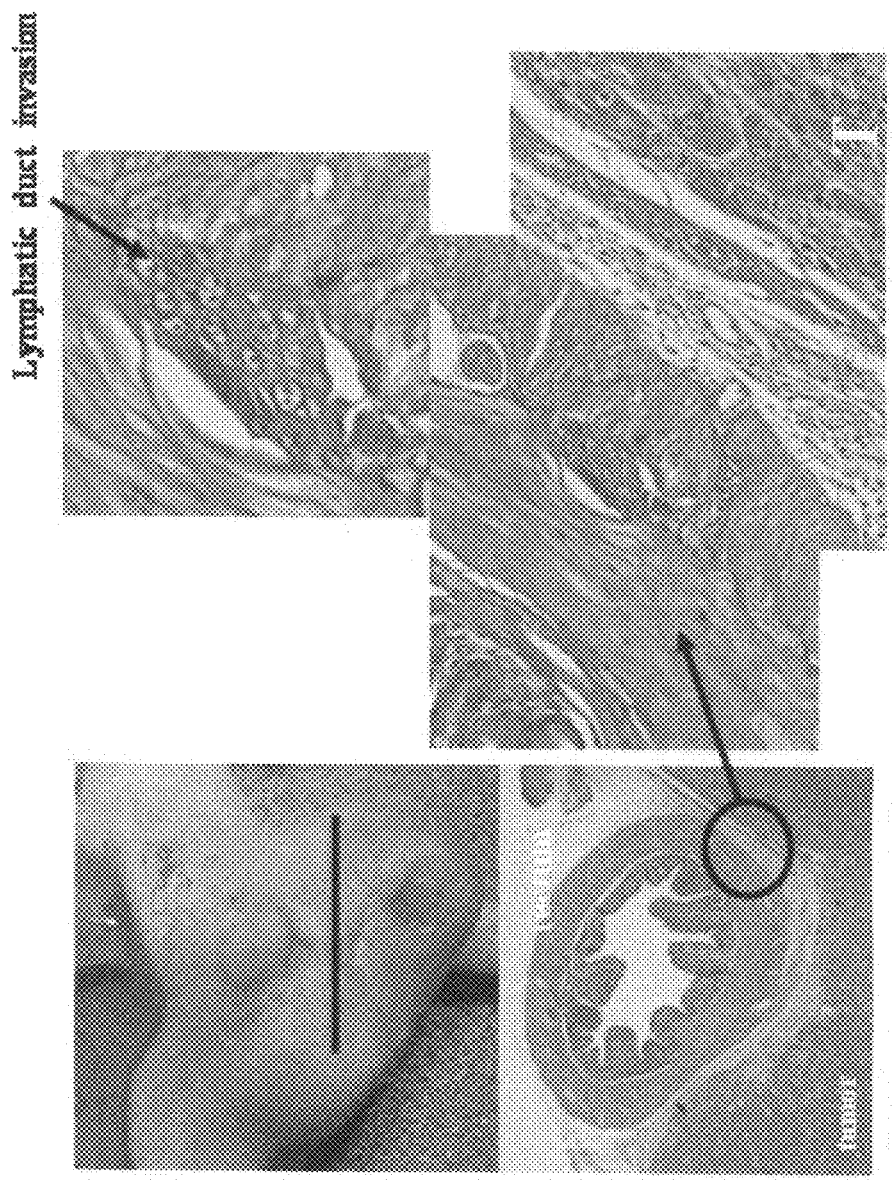
FIG. 16 is a diagram showing histological analysis in an orthotopic rectal cancer model using nude mouse and HT29 human large colon cancer cells.

As a result, tumor was formed around the rectum, and tumor cell mass could be confirmed in lymph vessels in the rectal wall (FIG. 16).

Figure 17:
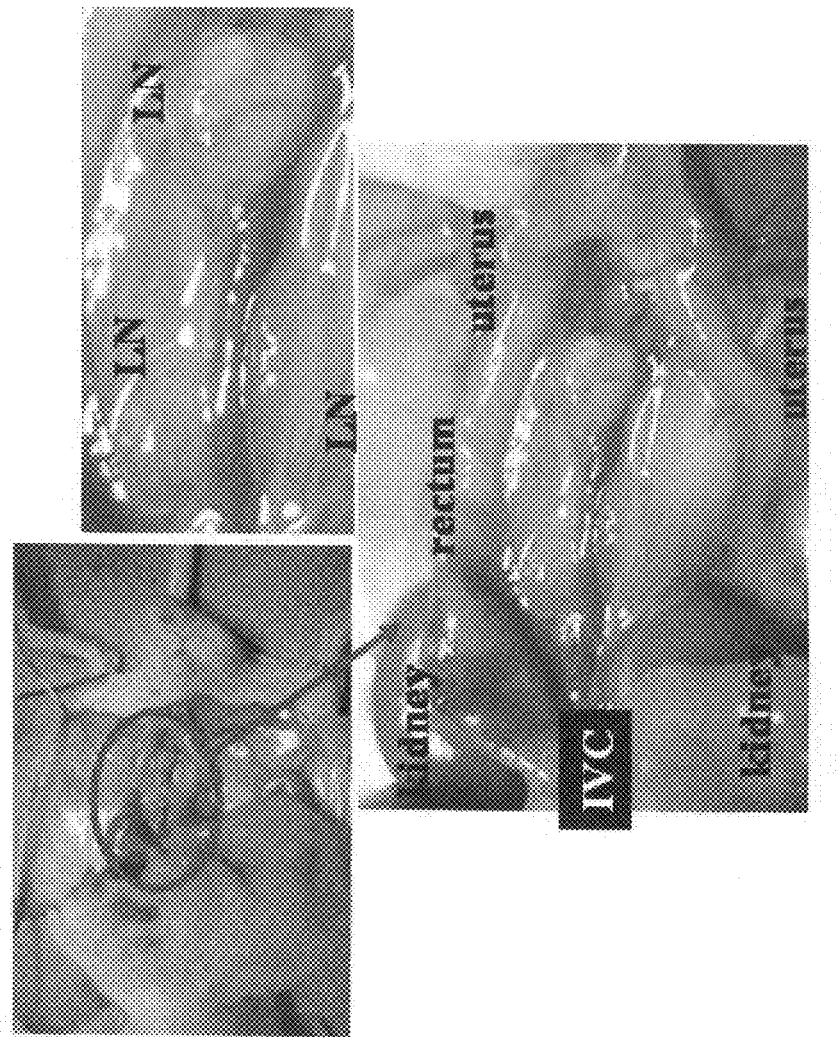
FIG. 17 is a diagram showing ventrotomy findings in an orthotopic rectal cancer model using nude mouse and HT29 human large colon cancer cells.

2. Ventrotomy Findings in Orthotopic Rectal Cancer Model Using Nude Mouse and HT29 Human Large Bowel Cancer Cell HT29 human large colon cancer cell was transplanted into the rectal wall, and ventrotomy was performed when gross tumor was formed. As a result, swelling was recognized in three lymph nodes (LN) around the aorta (FIG. 17)

Figure 18:
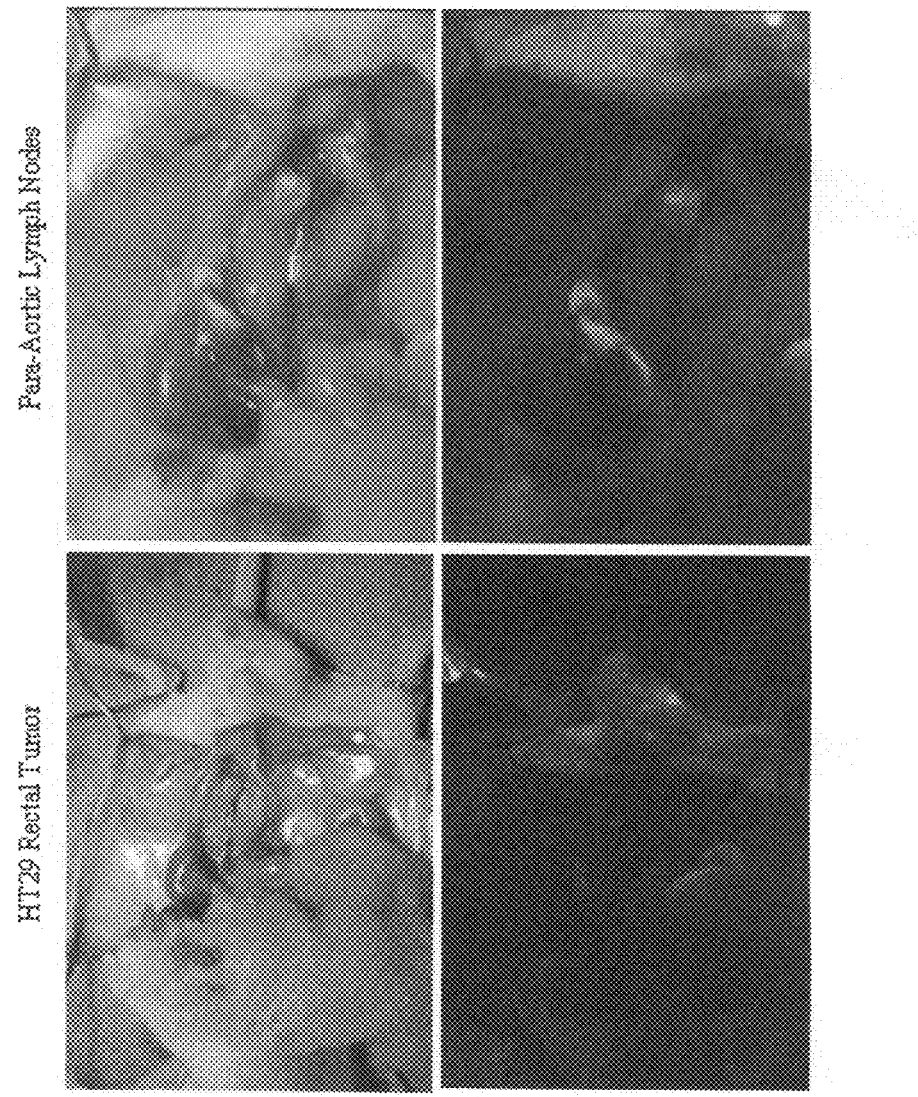
FIG. 18 is a diagram showing the intratumoral proliferation/replication of Telomelysin-GFP in HT29 rectal tumor and para-aortic lymph nodes observed by fluorescence imaging.

3. Detection of Intratumoral Proliferation/Replication of Telomelysin-GFP in HT29 Rectal Tumor and Para-Aortic Lymph Nodes by Fluorescence Imaging Expression of GFP fluorescence was recognized by fluorescence imaging with a CCD camera, in the transplanted HT29 rectal tumor and one of the three para-aortic lymph nodes (FIG. 18).

Figure 19:
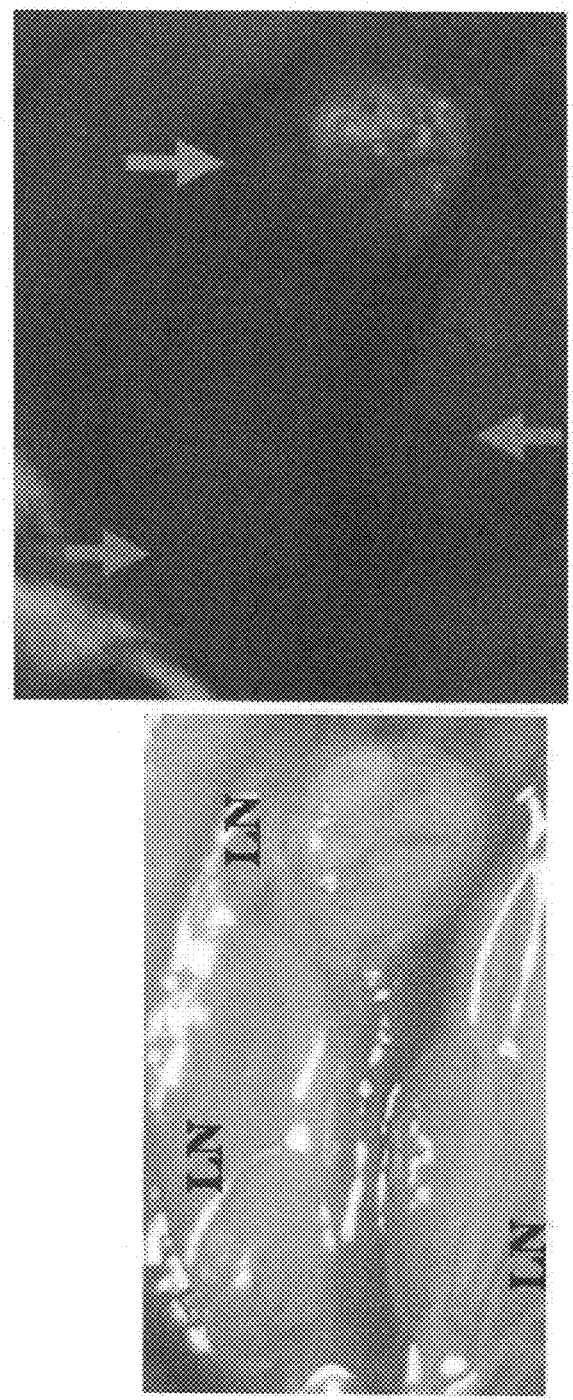
FIG. 19 is a diagram showing the intratumoral proliferation/replication of Telomelysin-GFP in para-aortic lymph nodes observed by fluorescence imaging.

4. Detection of Intratumoral Proliferation/Replication of Telomelysin-GFP in Para-Aortic Lymph Nodes by Fluorescence Imaging Expression of GFP fluorescence was recognized by fluorescence imaging with a CCD camera, in only one of the three para-aortic lymph nodes (FIG. 19).

Figure 20:
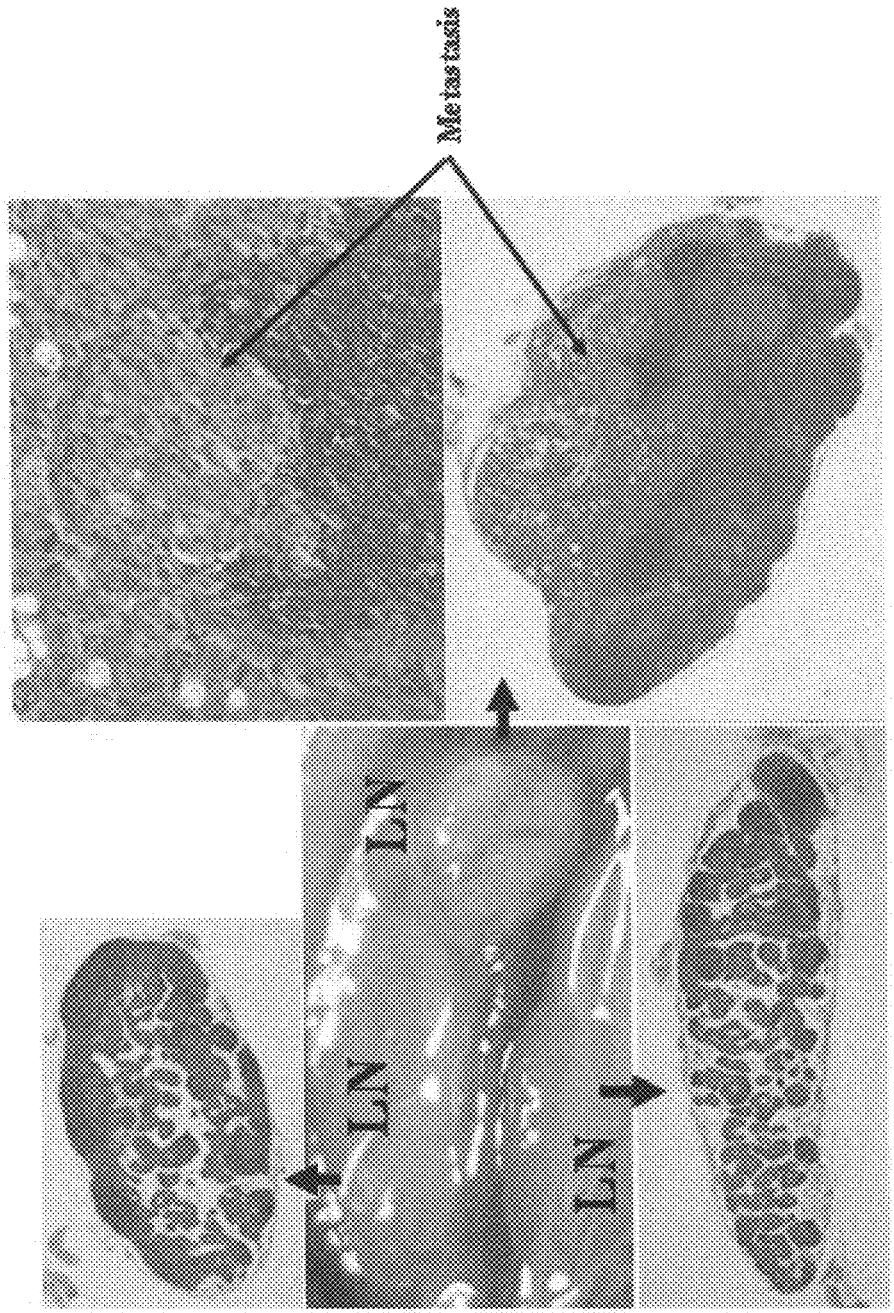
FIG. 20 is a diagram showing the intratumoral proliferation/replication of Telomelysin-GFP in para-aortic lymph nodes observed by fluorescence imaging.

5. Detection of Intratumoral Proliferation/Replication of Telomelysin-GFP in Para-Aortic Lymph Nodes by Fluorescence Imaging Histological analysis of para-aortic lymph nodes detected metastatic tumor tissue in the only one lymph node which was found GFP fluorescence-positive by fluorescence imaging with a CCD camera. Thus, it was confirmed that Telomelysin-GFP replicates only in metastasis-positive lymph nodes (FIG. 20).

REFERENCE

Reid T, Galanis E, Abbruzzese J, Sze D, Wein L M, Andrews J, Randlev B, Heise C, Uprichard M, Hatfield M, Rome L, Rubin J, Kirn D. Hepatic arterial infusion of a replication-selective oncolytic adenovirus (dl1520): phase II viral, immunologic, and clinical endpoints. Cancer Res 62 (21): 6070-9, 2002.

SEQUENCE LISTING FREE TEXT

SEQ ID NO: 5: Primer
SEQ ID NO: 6: Primer
SEQ ID NO: 7: Primer
SEQ ID NO: 8: Primer
SEQ ID NO: 9: Primer
SEQ ID NO: 10: Primer

What is claimed is:

1. A reagent for cancer cell detection, comprising a recombinant adenovirus where a replication cassette comprising an hTERT (human telomerase reverse transcriptase) promoter, an adenoviral E1A gene, an IRES sequence and an adenoviral E1B gene in this order is integrated in E1 region of the adenoviral genome and a labeling cassette comprising a gene encoding a GFP (green fluorescence protein) or an EGFP (enhanced green fluorescence protein) and a cytomegalovirus promoter operably linked to the gene encoding the GFP or the EGFP is integrated into the E3 region of the adenoviral genome such that the region encoding adenovirus death protein (ADP) is removed from the adenoviral genome, wherein the rest of the E3A and the E3B region are still present in the adenoviral genome.

2. The reagent according to claim 1, wherein the reagent is used for in vivo cancer detection or diagnosis, or for navigation surgery.

3. The reagent according to claim 1, wherein the hTERT promoter consists of the nucleotide sequence of SEQ ID NO:1, the adenoviral E1A gene consists of the nucleotide sequence of SEQ ID NO:2, the IRES sequence consists of the nucleotide sequence of SEQ ID NO:4, and the adenoviral E1B gene consists of the nucleotide sequence of SEQ ID NO:3.

* * * * *